(12) United States Patent
Tan

(10) Patent No.: US 10,159,516 B2
(45) Date of Patent: Dec. 25, 2018

(54) INTERCHANGEABLE ORTHOPEDIC BLADE

(71) Applicant: Virak Orthopedic Research LLC, Short Hills, NJ (US)

(72) Inventor: Virak Tan, Short Hills, NJ (US)

(73) Assignee: Virak Orthopedic Research, LLC, Short Hills, NJ (US)

( * ) Notice: Subject to any disclaimer, the term of this patent is extended or adjusted under 35 U.S.C. 154(b) by 325 days.

(21) Appl. No.: 14/712,051

(22) Filed: May 14, 2015

(65) Prior Publication Data

US 2016/0331425 A1 Nov. 17, 2016

(51) Int. Cl.
*A61B 17/80* (2006.01)
*A61B 17/68* (2006.01)
*A61B 17/74* (2006.01)
*A61B 17/86* (2006.01)

(52) U.S. Cl.
CPC .......... *A61B 17/8057* (2013.01); *A61B 17/68* (2013.01); *A61B 17/74* (2013.01); *A61B 17/746* (2013.01); *A61B 17/8615* (2013.01); *A61B 17/8625* (2013.01)

(58) Field of Classification Search
CPC ...... A61B 17/74; A61B 17/742; A61B 17/746
See application file for complete search history.

(56) References Cited

U.S. PATENT DOCUMENTS

| | | | |
|---|---|---|---|
| 2,699,774 A * | 1/1955 | Livingston | A61B 17/746 606/65 |
| 4,711,232 A | 12/1987 | Fischer et al. | |
| 4,938,773 A | 7/1990 | Strand | |
| 5,098,434 A | 3/1992 | Serbousek | |
| 5,889,906 A | 3/1999 | Chen | |
| 5,997,541 A | 12/1999 | Schenk | |
| 6,048,344 A | 4/2000 | Schenk | |
| 9,050,137 B2 * | 6/2015 | Tan | A61B 17/68 |
| 2008/0319489 A1 | 12/2008 | Triplett | |
| 2010/0168749 A1 | 7/2010 | Sidebotham et al. | |
| 2010/0268279 A1 | 10/2010 | Gabelberger et al. | |
| 2010/0312245 A1 | 12/2010 | Tipirneni | |
| 2010/0331895 A1 * | 12/2010 | Linke | A61B 17/74 606/304 |

* cited by examiner

*Primary Examiner* — Olivia C Chang
(74) *Attorney, Agent, or Firm* — Charles E. Baxley

(57) ABSTRACT

An interchangeable orthopedic blade including an internal portion and an external portion. The internal portion more accurately places the interchangeable orthopedic blade in, without excessive damage to, a bone when repairing a fracture in the bone and ultimately provide absolute stable fixation by the interchangeable orthopedic blade holding the fracture in its anatomic position and resisting applied forces while healing, to thereby provide a stable anatomic restoration and eliminate a need for revision surgery due to failure of fixation or malunion. The internal portion is received in the external portion and rotates relative to the external portion, but has the external portion move non-rotatably axially with the internal portion into the bone as the internal portion threads. In a first preferred embodiment, the internal portion is a screw with an externally threaded head. In a second preferred embodiment, the internal portion is an externally threaded set screw.

6 Claims, 27 Drawing Sheets

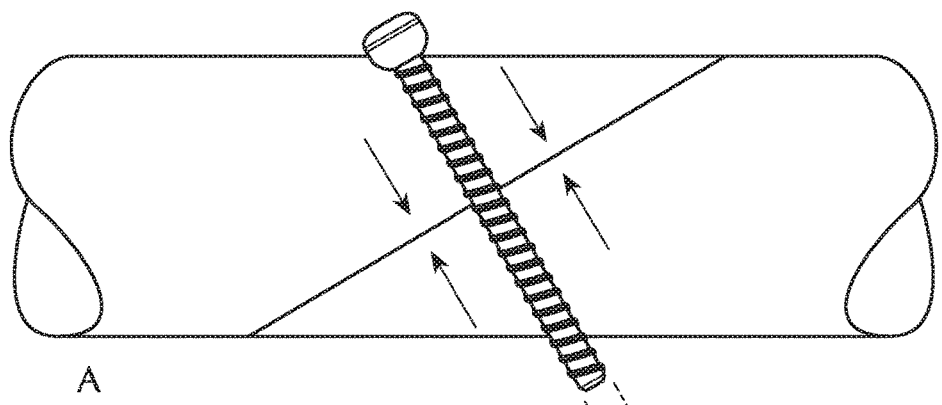
A
FIG. 8
PRIOR ART    4.5mm
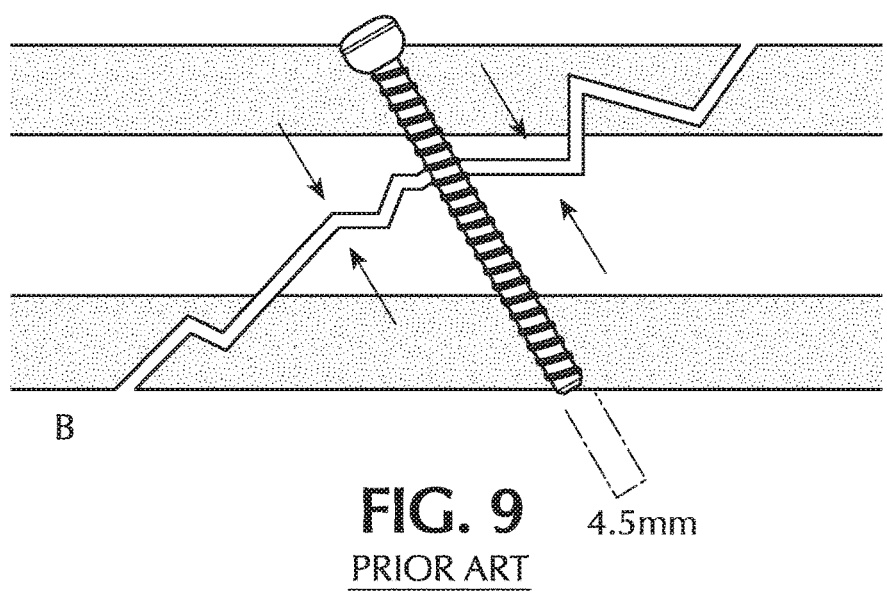
B
FIG. 9   4.5mm
PRIOR ART

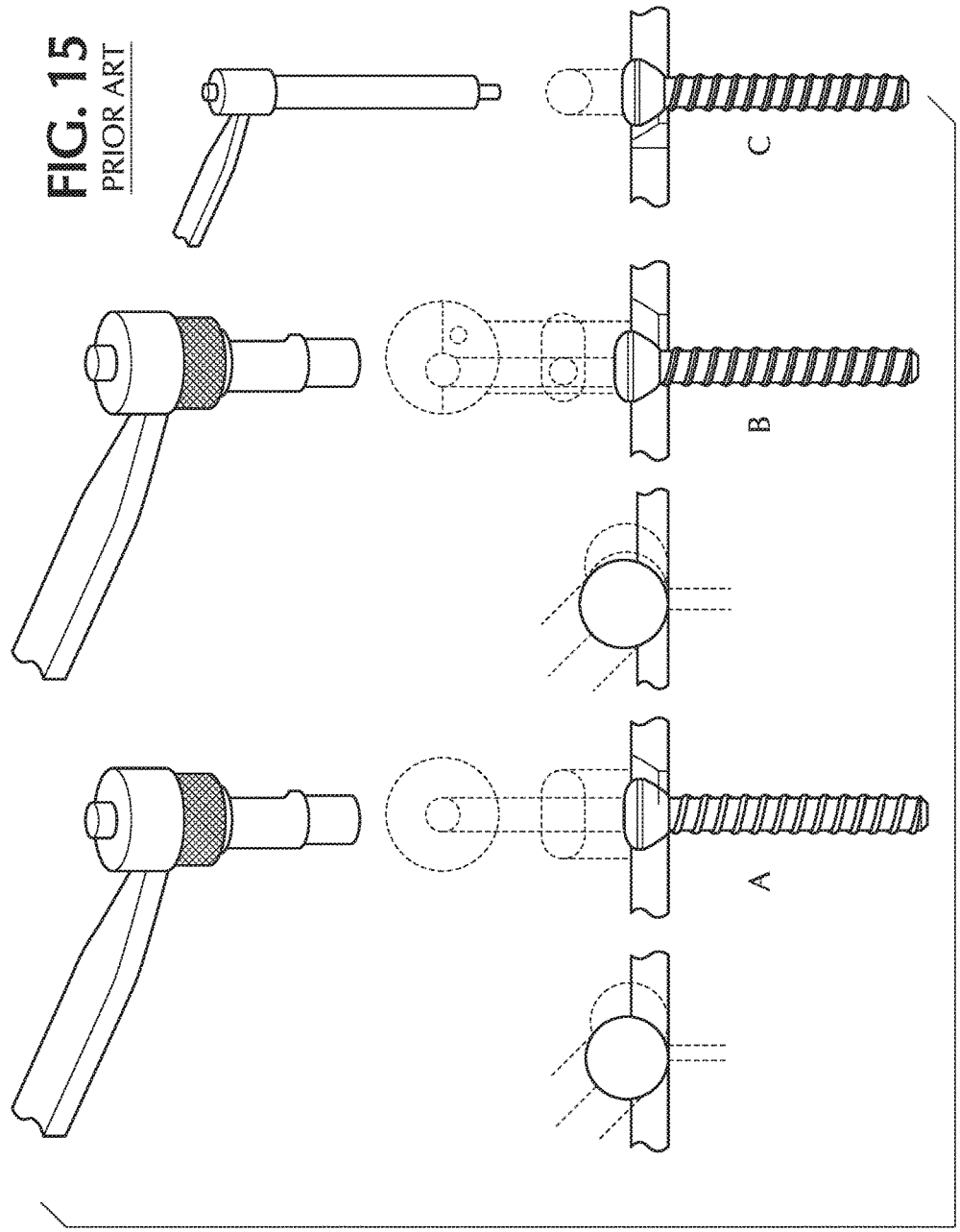

INTERCHANGEABLE ORTHOPEDIC BLADE

1. CROSS-REFERENCE TO RELATED APPLICATION

The instant non-provisional patent application is a Continuation-In-Part application of non-provisional patent application Ser. No. 13/550,955, filed on Jul. 17 2012, entitled INTERCHANGEABLE ORTHOPEDIC BLADE, and which claims the benefit of provisional patent application No. 61/689,402, filed on Jun. 4, 2012, and entitled INTERCHANGEABLE ORTHOPEDIC BLADE.

2. BACKGROUND OF THE INVENTION

A. Field of the Invention

The embodiments of the present invention relate to an orthopedic blade, and more particularly, the embodiments of the present invention relate to an interchangeable orthopedic blade for more accurately placing in, without excessive damage to, a bone when repairing a fracture in the bone by cooperating with an interchangeable orthopedic plate, so as to provide absolute stable fixation by holding the fracture in its anatomic position and resist applied forces while healing, to thereby provide a stable anatomic restoration and eliminate a need for revision surgery due to failure of fixation or malunion.

B. Description of the Prior Art (1) General Principles of Internal Fixation.

(a) History of Fracture Treatment.

Fractures have been treated with immobilization, traction, amputation, and internal fixation throughout history. Immobilization by casting, bracing, or splinting a joint above and below the fracture was used for most long bone fractures, with the exception of the femur for which traction was the mainstay of treatment. In the past, open fractures and ballistic wounds with long bone fractures were not amenable to standard fracture care because of the associated soft tissue injury and the difficulty in preventing sepsis. Thus, they usually resulted in amputation, especially during the US Civil War.

Although the concept of internal fixation dates back to the mid 1800s, Lister introduced open reduction and internal fixation ("ORIF") of patella fractures in the 1860s. Use of plates, screws, and wires was first documented in the 1880s and 1890s. Early surgical fixation initially was complicated by many obstacles, such as infection, poorly conceived implants and techniques, metal allergy, and a limited understanding of the biology and mechanics of fracture healing. During the 1950s, Danis and Muller began to define the principles and techniques of internal fixation. Over the past 40 years, advancements in biological and mechanical science have led to contemporary fixation theories and techniques.

(b) Introduction to Fracture Repair Biology.

Disruption of the endosteal and periosteal blood supply occurs with the initial trauma. Maintaining adequate blood supply to the fracture site is essential for healing. Hunter described the four classic stages of natural bone repair: inflammation; soft callus; hard callus; and remodeling. The inflammation stage begins soon after injury and appears clinically as swelling, pain, erythema, and heat. Disrupted local vascular supply at the injured site creates a hematoma and prompts the migration of inflammatory cells that stimulate angiogenesis and cell proliferation. After the initial inflammatory phase, the soft callus stage begins with an infiltration of fibrous tissue and chondroblasts surrounding the fracture site. The replacement of the hematoma by this structural network adds stability to the fracture site.

Soft callus is then converted into rigid bone, the hard callus stage, by enchondral ossification and intramembranous bone formation. Once the fracture has united, the process of remodeling begins. Fibrous bone is eventually replaced by lamellar bone. Although this process has been called secondary bone union or indirect fracture repair, it is the natural and expected way fractures heal. Fractures with less than an anatomic reduction and less rigid fixation—i.e., those with large gaps and low strain via external fixator, casting, and intramedullary ("IM") nailing—heal with callous formation or secondary healing with progression through several different tissue types and eventual remodeling. Anatomic reduction and absolute stabilization of a fracture by internal fixation alter the biology of fracture healing by diminishing strain—elongation force—on the healing tissue at the fracture site. Absolute stability with no fracture gap—e.g., via ORIF using interfragmental compression and plating—presents a low strain and results in primary healing—cutting cone—without the production of callus. In this model, cutter heads of the osteons reach the fracture and cross it where bone-to-bone contact exists. This produces union by interdigitation of these newly formed osteons bridging the gap. The small gaps between fragments fill with membranous bone that remodels into cortical bone as long as the strain applied to these tissues does not cause excessive disruption and fibrous tissue develops—nonunion. This method of bone healing is known as direct bone healing or primary bone union. Essentially, the process of bone remodeling allows bone to respond to the stresses to which it is exposed.

Based on the mechanical milieu of the fracture as dictated by the surgeon's choice of internal fixation and the fracture pattern, two patterns of stability can result that determine the type of bone healing that will occur. Absolute stability—i.e., no motion between fracture fragments—results in direct or primary bone healing—remodeling. Relative stability—i.e., a certain amount of fragment motion—heals with secondary or indirect bone union.

(c) Pins and Wires.

Kirschner wires—K-wires, 0.6-3.0 mm—and Steinmann pins—3-6 mm—have a variety of uses from skeletal traction to provisional and definitive fracture fixation. Resistance to bending with wires is minimal so they are usually supplemented with other stabilization methods when used for fracture fixation, but most commonly, wires are utilized as provisional fixation prior to definitive fixation with a stronger device. Skeletal traction with K-wires is possible with the use of a K-wire tensioner that with application stiffens the wire and allows it to resist bending load.

K-wires and Steinmann pins can provide provisional fixation for reconstruction of fractures, while incurring minimal bone and soft tissue damage and leaving room for additional hardware placement. Planning pin placement is important to avoid the eventual permanent fixation devices, and if possible, pins should be placed parallel to screws used for fracture compression. Depending on the diameter, pins may also be used as guidewires for cannulated screw fixation.

Permanent fixation options include fractures in which loading is minimal or protected with other stabilization devices, such as external fixators, plates, and braces. Pin or wire fixation is often used for fractures of the phalanges, metacarpals, metatarsals, proximal humeri, and wrists. K-wires commonly supplement tension-band wire constructs at olecranon, patella, and medial malleolus fractures.

The K-wires can be fully threaded or nonthreaded, and have either diamond or trocar points that are simplistic in design and have limited ability to cut hard bone—a process that can lead to overheating. For this reason, they should be inserted slowly when power equipment is used to avoid thermal necrosis. Image intensifiers are often used for optimal positioning of the fixation, especially with percutaneous insertion combined with closed reduction techniques. The pins may have points at both ends, facilitating antegrade-retrograde fixation techniques. They are, however, a potential hazard and should be used with caution.

Steinmann pins are larger, may be threaded or unthreaded, and are currently used primarily for long bone traction in conjunction with a Bailer traction stirrup. Early techniques of fracture treatment consisting of pins for skeletal traction and incorporation into a cast were fraught with pin infections, loosening, and loss of reduction. This technique has been replaced with more advanced external fixation devices, internal fixation methods, and minimally invasive plating and IM devices.

Guidewires for cannulated screws are employed at times for definitive fixation as they are terminally threaded allowing for fixation on the opposite cortex. An example of this would be the closed reduction and percutaneous pinning technique for proximal humeral fractures.

(d) Screws.

Bone screws are a basic part of modern internal fixation. They can be used independently or in combination with particular types of implants. The common design of a screw consists of a tip, shaft, thread, and head, as shown in FIGS. 1-3. A round screw tip requires pretapping, whereas a fluted screw tip is self-tapping. The screw shaft is located between the head and the threaded portion of the screw. The screw thread is defined by its major or outside thread diameter and minor or root shaft diameters, pitch, lead, and number of threads. The distance between adjacent threads is the pitch.

The lead is the distance a screw advances with a complete turn. Lead is the same as pitch if the screw is single threaded, and lead is twice the pitch if the screw is double threaded—faster screw insertion. The root diameter determines the screw's resistance to breakage—tensile strength. Screws are referred to by their outer thread diameters, bone type for intended use—cortical or cancellous determined by pitch and major/minor diameters—and proportion of thread—partially or fully threaded.

Screw pullout strength can be affected by several factors. Bone composition density—is the primary determinant of screw fixation. The total surface area of thread contact to bone—root area—is another factor in pullout resistance. Pretapping the screw hole theoretically reduces microfracture at the thread-bone interface, but requires an extra step for insertion. Self-tapping screws have been shown to have no clinical difference from pretapped screws for fracture or plate fixation, eliminate the tapping step, and are now the industry standard. The fluted portion of the screw tip has less thread contact with the bone so slight protrusion at the opposite cortex is recommended.

Pitch—the distance between adjacent threads—affects purchase strength in bone. Increasing the pitch increases bone material between the threads, but decreases the number of threads per unit of distance.

The industry standard for the screw head is a hexagonal recess that provides a large contact surface between the screw head and screwdriver and allows for optimal transmission of torque, as shown in FIG. 3. A cross-type screw head is used on some screws in the 2.0 and smaller screw—minifragment—sets. The star design or TORX head found in industry has been adapted to the screw heads for the Association for the Study of Internal Fixation ("AO/ASIF") locking plates, and has been shown to be superior for torque and resistance to stripping.

Several forces are involved with screw insertion and tightening. Torque is applied through the screwdriver to the screw head in a clockwise rotation to advance the screw in the predrilled path—or in the case of a cannulated screw—over a guidewire. This advancement produces a circumferential force along the thread. For cortical screws, the drill diameter is slightly larger than the root—shaft—diameter of the screw. Axial tension is created with impingement of the screw head on the cortex or plate generating tension through the screw. To optimize these forces, screws should ideally be inserted at 80% of the torque needed to cause them to strip. An estimated 2500-3000 newtons of axial compression force can be applied to the average screw. Over time, the amount of compressive force decreases slowly as the living bone remodels to the stress. The fracture healing time, however, is usually shorter than the time it takes for substantial loss of compression and fixation.

The two basic types of screws available for the variability of bone density are cortical and cancellous screws. Cortical screws are designed for compact diaphyseal bone, whereas cancellous screws are designed for the more trabecular metaphyseal bone. Cortical screws have a smaller major—thread—diameter, decreased pitch, and a shallower thread than cancellous screws. Standard nonlocking cortical screw diameter choices include 1.5, 2.0, 2.7, 3.5, and 4.5 mm.

Cancellous screws typically have a larger major—thread—diameter and pitch and a greater difference between major and minor—shaft—diameters in comparison to cortical screws providing more surface area for bone purchase. These screws are intended for use in metaphyseal fixation where bone is softer. Cancellous screws are available in sizes 4.0 and 6.5 mm, and cannulated sizes vary from 4.0-7.5 mm.

Tapping is not usually necessary in metaphyseal bone, as cancellous bone is porous relative to compact diaphyseal bone and usually requires only the initial pilot hole or cannulated screw guidewire. With subsequent screw insertion, there is compression of the bone along the path of the threads, which increases the local bone density in contact with the thread, thereby potentially increasing screw purchase. Tapping may be considered in strong metaphyseal bone to avoid stripping if advancement of the screw is difficult.

Positional or neutralization screws are to attach an implant, such as a plate, to bone by compression between the plate and bone, as shown in FIG. 4. This function is modified when the screw is used to lag across a fracture through the plate or when used for fracture compression, as with a dynamic compression screw. For a positional screw, the pilot hole is drilled with the appropriate-size bit—shaft diameter—for the screw to be inserted—e.g., a 3.2-mm drill bit for a 4.5-mm screw—using a centering guide for the plate hole. A depth gauge is used to determine appropriate screw length, and the thread cut is then made with an appropriate tap or without a tap when self-tapping screws are used or screws are placed in metaphyseal bone.

Interfragmentary lag screws provide compression across two bone surfaces using the lag technique. A lag screw is a form of static compression, and is applicable to intra-articular fractures to maintain reduction and diaphyseal fractures for stability and alignment. Ideally, lag screw fixation produces maximum interfragmentary compression when the screw is placed perpendicular to the fracture line, as shown in FIGS. 5-7. Most lag fixation techniques require additional stabilization to neutralize the axial bending and rotational forces applied to the bone during functional postoperative care. This is provided by a neutralization or buttress plate or external fixation.

If lag screws are to be used without neutralization plate fixation, especially in long spiral fractures>2 times the diameter of the involved bone—the ideal inclination of the screw is halfway between the perpendiculars to the fracture plane and to the long axis of the bone. Placing the screw perpendicular to the long axis of the bone can also be considered because longitudinal or shear compression may cause the screw or screws to tighten. Interfragmentary screw fixation alone may be appropriate for avulsion injuries in which shear forces generate metaphyseal and epiphyseal intra-articular fractures provided bone quality is good.

A fully threaded screw can serve as a lag screw with the near cortex over-drilled to the size of the screw's major—thread—diameter, 4.5 mm in the example, as shown in FIGS. 8 and 9. Once the near cortex is drilled, which provides a gliding hole, a drill sleeve with the outer diameter of the drill bit—4.5 mm—is inserted into the hole, and the standard drill bit—3.2 mm shaft diameter—is used to drill the far cortex. As the screw threads grasp the distal cortex, compressive forces are generated through the axis of the screw to the screw head causing the fracture fragments to be compressed. This same mechanical effect can be generated by a partially threaded screw, with all threads entirely within the opposite bony fragment.

Cannulated screws are now provided by most trauma manufactures in sizes from minifragment to 7.5 mm usually with a cancellous thread, but cortical patterns are also available as they are more commonly used in periarticular/metaphyseal bone. The guidewire is usually placed under fluoroscopic control, and allows for initial provisional fixation.

Cannulated screws allow for a percutaneous technique, such as is used with hip pinning, or may be used with limited open reduction techniques and can help minimize soft tissue dissection and periosteal stripping. Most designs are now self-drilling and self-tapping, but some may require predrilling over the guidewire with dense bone. The guidewires are usually terminally threaded—although nonthreaded are available—and when drilling over the wire, it is recommended not to drill over the threaded portion because the guidewire may be inadvertently removed along with removal of the drill bit. This could result in difficulty relocating the drill hole through soft tissue or loss of provisional fixation.

The pullout strength of cannulated 7-mm cancellous screws versus 7-mm noncannulated screws and 3.5-mm cannulated and noncannulated screws has been tested in two studies, and no significant difference was noted regarding pullout strength. These studies, however, are specific to these screw designs and similar fixation properties cannot necessarily be applied to other screw designs and sizes. It should also be considered that the relative costs of cannulated screws are often ten times that of similar-sized noncannulated screws. Therefore, noncannulated screws should be used when technically feasible.

Self-tapping screws have the advantage of eliminating a step during screw insertion, thereby decreasing operative time. The fluted design of the screw cuts a sharp path in the predrilled hole eliminating the need for tapping. Baumgart and associates showed that insertion torque and pullout strength were comparable for tapped and self-tapping screws. Only if the cutting tip did not protrude through the second cortex did they find a reduction of pullout strength of approximately 10%.

Schatzker and associates went on to prove that self-tapping screws inserted at 80% of thread-stripping torque, and then removed and reinserted twelve times did not lose any significant holding power. When inserting a self-tapping screw as a lag screw, care should be taken with technique to avoid missing the opposite cortex as these screws are often at an angle to the diaphyseal shaft or there may be difficulties with advancing the screw while also tapping, especially with hard cortical bone. It is not unreasonable to consider tapping this opposite cortex first to help with alignment and advancement of the lag screw.

Locked screws are incorporated in more recent plate designs, and may be inserted as unicortical or bi-cortical screws depending on the type of plate and fracture. These screws—with reduced pitch—produce minimal axial force—if any—and provide biomechanical fixation by locking the screw head into the plate with a tapered thread perpendicular to the plate. Some newer designs allow for some variable angulation of the locking screws. The system acts generally like an internal-external fixator, as shown in FIGS. 10 and 11. These systems are discussed further in Plates below.

(e) Plate Types.

Plates are provided in various sizes and shapes for different bones and locations. Dynamic compression plates ("DCPs") are available in 3.5 mm and 4.5 mm sizes. The screw holes in a DCP are shaped with an angle of inclination on one side away from the center of the plate. When tightened, the screw head slides down the inclination causing movement of the bone fragment relative to the plate, as shown in FIG. 12. As one bone fragment approaches the other at the fracture, compression occurs. The shape of the holes in the plate allow for 25° of inclination in the longitudinal plane and 7° inclination in the transverse plane for screw insertion.

The dynamic compression principle requires that the holes of the plate be shaped like an inclined and transverse cylinder. Like a ball, the screw head slides down the inclined cylinder. Because the screw head is fixed to the bone via the shaft, it can only move vertically relative to the bone. The horizontal movement of the head as it impacts the angled side of the hole, results in movement of the bone fragment relative to the plate, and leads to compression of the fracture.

Limited-contact DCPs ("LC-DCPs") were designed to limit possible stress shielding and vascular compromise by decreasing plate-to-bone contact by 50%, as shown in FIG. 13.

Theoretically, this leads to improved cortical perfusion with increased preservation of the periosteal vascular network, and reduces osteoporosis under the plate. The regular DCP has an area of decreased stiffness located at the plate holes, and with bending, has a tendency to bend at the holes with a segmented pattern, whereas the LC-DCP—with a different geometric design incorporating the holes and plate undersurface—allows for gentle bending distributed throughout the plate, as shown in FIGS. 14A and 14B.

Finally, the LC-DCP is designed with plate hole symmetry providing the option of dynamic compression from either side of the hole, and allowing compression at several levels. In general, standard DCP style plates were replaced years ago with updated designs by most manufacturers with variations on the LC-DCPs, and in turn, these plates have been replaced by all manufacturers with plates capable of both locking and nonlocking functions. Some specific nonlocking-style plates are still retained in use as they function well for a variety of specific fractures, such as the one-third tubular plate for lateral malleolar fractures and the 3.5 mm recon plates for periacetabular fixation.

Techniques for the application of both the DCP and LC-DCP are the same, as shown in FIG. 15. Screws can be inserted in neutral position or a compression position depending on the desired mechanical result. The DCP uses a green guide to insert a neutral screw, which adds some compression to the fracture owing to the 0.1-mm offset. The gold guide produces a hole 1 mm off-center, away from the fracture, and allows for 1 mm of compression at the fracture site with tightening of the screw. The LC-DCP universal drill guide allows for either neutral or eccentric placement of screws. When creating an eccentric hole to one side or another, the guide is slid to the end of the plate hole without applying pressure, and the hole is drilled. By placing pressure against the bone with the drill guide, the spring-loaded mechanism allows for centralization of the hole for neutral screws—particularly if the screw must be inserted at an angle to the plate.

The 3.5 one-third tubular plate is 1 mm thick and allows for limited stability, as shown in FIG. 16. The thin design allows for easy 2-dimensional contouring and is primarily used on the lateral malleolus, and on occasion, the distal ulna. The oval holes allow for limited fracture compression with eccentric screw placement.

Improvements by all manufacturers have been made for plates used for almost all areas of the body that require placement of a plate near a joint and over extended areas of diaphyseal bone. The refinement of contour—along with screw head modification reduces hardware prominence and increases fixation options.

The 95°-angled plates are useful in the repair of metaphyseal fractures and reconstruction of the femur as they provide very rigid fixation, as shown in FIGS. 17A-17D. They are technically demanding, and proper insertion requires the blade to be inserted with consideration of 3 dimensions—i.e., vagus/valgus angulation, anterior/posterior position, and flexion/extension rotation of plate. The screw barrel devices are considered somewhat easier to insert because the flexion/extension of the plate is correctable after insertion of the screw.

Reconstruction plates are thicker than one-third tubular plates, but they are not quite as thick as DCPs, as shown in FIGS. 18A and 18B. Designed with deep notches between the holes, they can be contoured in three planes to fit complex surfaces—e.g., around the pelvis and acetabulum. Reconstruction plates are provided in straight and slightly thicker and stiffer precurved lengths. As with tubular plates, they have oval screw holes allowing potential for limited compression.

Cable plates incorporate a large fragment plate with cerclage wires to be used with a tensioning device. These are used primarily with femoral fractures surrounding or adjacent to prosthetics—femoral hip or knee implants. Cortical allograft struts are often incorporated for osteoporotic bone.

(f) Plate Functions.

Standard plate fixation requires exposure of the fracture site, hematoma evacuation, and reduction of the fracture with possible interfragmentary lag fixation. After a fracture occurs, the periosteal blood supply is dominant, and this network of connective tissue must be preserved to optimize healing. Excessive periosteal stripping and careless soft tissue techniques can impair local blood supply and prolong healing.

Diaphyseal plate fixation associated with an anatomic reduction and interfragmentary compression provides absolute stability. Plates are often indicated in articular fractures to neutralize the axial forces on the interfragmentary screws compressing cancellous bone to facilitate its healing. A fracture anatomically reduced without a gap and fixed with absolute stable fixation will undergo primary healing.

Dead bone at the fracture site is resorbed by osteoclasts of the cutting cones as these cells traverse the fracture site. The osteoclasts are closely followed by ingrowth of blood vessels and mesenchymal cells and osteoblast infiltration. Stress shielding of the bone is rarely caused by the plate relieving axial load to the bone. Plate-induced osteoporosis is caused by disruption of the local vascularity to the bone cortex secondary to an impediment of centrifugal cortical blood flow by the plate.

Osteoporosis under a plate should be kept in mind after removal of hardware because the bone also has the mechanical disadvantage of empty screw holes. This vascular-caused cancellization of the cortical bone in diaphyseal areas usually resolves within two years of plate application so it is safe to remove a plate at this time with the refracture rate being minimal. Plates applied to metaphyseal areas may have the option of earlier removal depending on the amount of diaphyseal extension and healing.

Bridge plating is used for comminuted unstable fractures in which anatomic restoration and absolute stability cannot be achieved. Minimal exposure and indirect reduction techniques are used to preserve the blood supply to the fracture fragments for healing, and a plate is attached to the two main fragments spanning the area of fracture. The plate is used to provide proper length, axial alignment, and rotation, but it is obviously limited for any load.

With more recent advances of combining minimally invasive plate techniques utilizing locking plate technology, plate devices act more as an internal fixator. This approach began in 2001 with the Less Invasive Surgical Stabilization ("LISS") plate that is advanced in the submuscular tissue through a small incision over the periosteum, but does not necessarily contact the bone along the length of the plate. This technique limits the disruption of periosteal blood supply that is seen in conventional plating systems as the fixation is through the locking screws, thereby not necessitating compression to the plate for stability. The early development of this concept with the Point Contact Fixator ("PC-Fix") system in the 1990s—and then later with LISS—takes advantage of unicortical, self-drilling, and self-tapping screws with threaded screw heads that lock into the screw hole of the plate and minimize soft tissue disruption.

Once the LISS plate is aligned with the central shaft of the bone, screw placement can be accomplished percutaneously with a radiolucent guide attachment to the plate. Unicortical screws are recommended for use in diaphyseal bone, with longer screws for use in the metaphyseal area, thereby functioning as a fixed-angle device.

Currently, most manufacturers offer new locking plate products. These devices range from standard straight plates of all sizes with locking and standard screws to anatomically specific plates that act as fixed-angle devices. These new plate designs incorporate improved contour with locking screw options for fixation offering significant advantages over the conventional designs for certain fractures. Proximal and distal humerus, distal radius, distal femoral, and proximal—bicondylar—and distal tibial fractures are examples of injuries that benefit from this technology having the improved ability to hold a fracture in its anatomic position and resist applied forces while healing. Conventional plates—that rely on friction forces against the plate from screw fixation and buttressing in metaphyseal and articular fractures—are limited in resisting applied loads versus locking fixation.

In contrast, certain shaft fractures with stable patterns and adequate room for fixation have proven high union rates with conventional plating—humeral shaft, radius, and ulna shaft—and any significant difference between the two techniques is difficult to realize with proper surgical technique. Current recommendations are to use locking screws in situations with limited fixation options, osteoporotic bone, or need for fixed-angle support. For example, a simple lateral plateau fracture that requires buttress fixation and with which the bone quality is reasonable can be adequately treated with a conventional nonlocking lateral plate.

Currently, most LC-DCP small and large conventional plate sets have been reduced as utilization of specialty plates has increased with periarticular design and locking capability, the surgeon deciding which screws are locking or nonlocking depending on the fracture. As with cannulated screws, locking screws can vary in cost ranging from 8-15 times the cost of a conventional screw, and therefore should be used when needed based on the fracture pattern and expected loads. This cost issue is lessened to some degree when taking into account the need for revision surgery due to failure of fixation or malunion. Thus, a balance of usage guided by conventional wisdom, common sense, and biomechanical and outcome studies is recommended.

(g) Tension-Band Principle.

Plates and other constructs can be used to function as a tension-band if an eccentrically loaded bone—e.g., the femur—has the device placed on the tension-convex side of the bone. Using load-strain diagrams, Frederic Pauwels—who first described the tension-band concept—showed that a curved tubular structure placed under an axial load had a tension side and a compression side. With this theory, he described the application of internal fixation on the tension side to convert tensile forces into compressive forces at the fracture site.

With static compression applied by the implant—e.g., tensioning of wire compression with plate—dynamic compression then develops with joint flexion as with a patella or olecranon fracture or with load as with lateral femoral plating, as shown in FIGS. 19A and 19B. With this technique, the internal fixation device must have the strength to withstand the tensile distraction forces created by muscles during motion, and the bone on the opposite side of the plate must be able to withstand the compressive forces as a medial buttress.

Wires and plates are usually quite strong under pure tension forces, but with bending forces added fatigue can occur rapidly. If bony support is compromised on the cortex, opposite from the tension device—e.g., from fragmentation, osteoporosis—bending stresses can develop causing failure of fixation. Wiring techniques commonly include longitudinal K-wires for rotational and axial alignment control in the case of bone fragmentation.

Conversely, fixation on the concave side of the bone occurs in rare situations, such as with medial plating of a femur or anterior plating of the humerus. In these situations, fractures have minimal resistance to bending stresses, and gapping can occur on the convex side resulting in failure of fixation, as shown in FIG. 20. Therefore, attempts should be made to limit potential bending forces to fixation to prevent fixation failure. The tension-band principle can be applied to wires, cables, sutures, plates, and external fixators as long as the basic principles are followed.

(2) Angled Plates.

(a) General Principles.

In 1959, the AO developed the angled plates, as shown in FIGS. 21 and 22. The "U" profile was chosen for the blade portion, and a single blade unit with a fixed angle between the blade and the plate was adopted in preference to the two-piece variable angle devices. The advantage of the fixed angle is the increased strength and the increased corrosion resistance of the implant. The disadvantage is the increased difficulty of insertion. In the proximal femur, the blade has to be inserted in the middle of the femoral neck and at a predetermined angle to the shaft axis. In addition, the plate portion of the angled blade plate has to be inserted so that it will line up with the axis of the shaft at the end of the procedure. In the distal femur, the blade has to line up with the joint axis and with the inclination of the patellofemoral joint and be inserted exactly into the middle of the anterior half of the femoral condyles at a predetermined distance from the joint, and the plate has to line up with the axis of the femoral shaft. Because of these technical complexities, a preoperative plan—including a preoperative drawing—is essential so that the operation can follow it step-by-step. The surgeon must also exercise great care at the time of surgery and pay particular attention to anatomic landmarks, position, and inclination of the implants in order to follow the preoperative plan. This usually ensures that at the end of the procedure, everything fits and that the desired end result is achieved.

(b) Preoperative Planning

An X-ray of the normal side is required in order to have a template on which to plan the procedure. For the proximal femur, the X-ray must be taken with the hip in 15°-20° internal rotation to correct for ante-version. For the distal femur, accurate antero-posterior and lateral X-rays centered on the joint are necessary. The outlines of the proximal or the distal femur are drawn in, as are all the fracture lines. The fracture pattern determines the steps of the internal fixation, as well as the choice of plate. The selected plate is drawn in with the help of the templates. The plan should include the order in which the different steps will be carried out, should denote the function of the different screws, should indicate if a gliding hole or a thread hole needs to be predrilled before the reduction is carried out, and whether a bone graft is necessary. All the guide wires that are necessary to execute the procedure must also be shown, and their function and inclination carefully noted Schatzker rationale.

These working drawings are necessary before any surgical procedure is embarked upon. They are of particular importance before corrective osteotomies because they are the only way the surgeon can check preoperatively the result of the osteotomy, as well as the three-dimensional concept of the procedure.

(c) Implants and Instruments.

A number of specialized instruments have been developed that greatly facilitate the exact execution of the operation in accordance with the preoperative plan. Neither an X-ray nor an image intensifier is a substitute for a three-dimensional concept of the local anatomy, nor will they serve as a guide to the correct insertion of the guide wires. Correct insertion is based on the anatomic landmarks and on the particular device employed for fixation. The X-ray or the image intensifier are, however, useful to verify the definitive insertion of the seating chisel or of the specialized guide wire for the dynamic hip or condylar screw. An X-ray is also useful as a permanent intra-operative record of the position of the guide wires and of all the internal devices, as well as of the position of an osteotomy if one is being carried out.

(d) The Angled Plates for the Proximal and Distal Femur.

Initially, as shown in FIG. 21, the AO developed the 130° plate for use in the proximal femur, and, as shown in FIG. 22, the condylar blade plate is for use in the distal femur. With time it became evident that the condylar plate could also be used for the treatment of certain inter-rochanteric and subtrochanteric fractures of the proximal femur. Following further modifications and refinements, the AO has developed the dynamic hip screw ("DHS") and the dynamic condylar screw ("DCS"). These two have almost replaced the "U" profile angled blade plates in the treatment of fractures, but the latter continue to be used in reconstructive surgery, such as osteotomies. The original fixed angle devices are described in detail because all the specific features, indications, and anatomic considerations apply in exactly the same way as to the DHS and to the DCS.

The 130° angled plate has a blade with a "U" profile, as shown in FIG. 21. The plate portion comes in varying lengths depending on the particular fracture to be fixed. Thus, the four- or six-hole plates are used for most inter-trochanteric fractures, and the plates—9-12 holes—for sub-trochanteric fractures.

The condylar plate has a fixed angle of 95° between its blade and plate portion, as shown in FIG. 22. The shortest plate available has five holes. The length to be used will vary with the fracture pattern. The shortest blade is 50 cm, and the length of the blade chosen will depend on the size of the femur and whether the plate is being used in the distal or proximal femur.

Numerous innovations for osteosynthetic devices have been provided in the prior art, which will be described below in chronological order to show advancement in the art, and which are incorporated entirely herein by reference thereto. Even though these innovations may be suitable for the specific individual purposes to which they address, nevertheless, they differ from the embodiments of the present invention in that they do not teach an interchangeable orthopedic blade for more accurately placing in, without excessive damage to, a bone when repairing a fracture in the bone by cooperating with interchangeable orthopedic plate, so as to provide absolute stable fixation by holding the fracture in its anatomic position and resist applied forces while healing, to thereby provide a stable anatomic restoration and eliminate a need for revision surgery due to failure of fixation or malunion.

(1) U.S. Pat. No. 4,711,232 to Fischer et al.

U.S. Pat. No. 4,711,232—issued to Fischer et al. on Dec. 8, 1987 in U.S. class 606 and subclass 67—teaches a fastener for anchoring in a bore in a bone, which has a screw with a substantially cylindrical outer surface formed with a helical screw thread. The screw has at its screw thread, a thread diameter, and between the turns of the thread at the surface, a root diameter smaller than the thread diameter. A synthetic-resin anchor sleeve of a resilient fitted in the bore is of an outside diameter corresponding generally to the diameter of the bore, and has an outer end formed with an outwardly open polygonal-section recess, an inner end formed with an inwardly open and transversely through-going slot, an outer end portion of an inside diameter greater than the root diameter but smaller than the thread diameter, an inner end portion of an inside diameter smaller than the root diameter, and an external helicoidal screw thread extending about two-thirds of the length of the sleeve from its inner end toward its outer end.

(2) U.S. Pat. No. 5,098,434 to Serbousek.

U.S. Pat. No. 5,098,434—issued to Serbousek on Mar. 24, 1992 in U.S. class 606 and subclass 308—teaches a bone screw for joining bone fragments or for mounting a prosthetic component onto an underlying bone. The bone screw includes a head and an elongated cylindrical shank that is integral with, and extends from, the head. The shank includes a threaded member and a shoulder member connecting the threaded member and the head. The shoulder member has an outer surface with a porous medium thereon for encouraging bone ingrowth fixation. The outer diameter of the shoulder member is greater than the diameter of a bore of the bone into which the screw is to be threadedly engaged. The head of the screw is provided with a coupling member engageable by a tool for selectively rotating the shank to advance the screw into the bone. As the bone screw is advanced toward a fully seated position, the shoulder member with the porous medium thereon engages the bone in a fitting manner that is described as a "scratch fit." Initial loosening of the bone screw due to the viscoelastic relaxation of the bone tissue following fixation is thereby largely inhibited and long term loosening of the bone screw is also inhibited by providing an interface onto which, or into which, bone tissue can grow to stabilize the repair site or the implanted component.

(3) U.S. Pat. No. 5,899,906 to Schenk.

U.S. Pat. No. 5,899,906—issued to Schenk on May 4, 1999 in U.S. class 606 and subclass 301—teaches a threaded washer having a central bore for use with a bone screw. The washer is threaded into a counterbore extending below the bone surface and into cancellous bone material. The external washer threads are tapered. The bone screw is inserted through the central bore of the washer and threaded into the fragment beyond the fracture. The washer permits the bone screw head to be located beneath the bone surface.

(4) U.S. Pat. No. 5,997,541 to Schenk.

U.S. Pat. No. 5,997,541—issued to Schenk on Dec. 7, 1999 in U.S. class 606 and subclass 303—teaches a threaded washer having a central bore for use with a bone screw. The washer is threaded into a counterbore extending below the bone surface and into cancellous bone material. The external washer threads are tapered. The bone screw is inserted through the central bore of the washer and threaded into the fragment beyond the fracture. The washer permits the bone screw head to be located beneath the bone surface.

(5) U.S. Pat. No. 6,048,344 to Schenk.

U.S. Pat. No. 6,048,344—issued to Schenk on Apr. 11, 2000 in U.S. class 606 and subclass 916—teaches a threaded washer having a central bore for use with a bone screw. The washer is threaded into a counterbore extending below the bone surface and into cancellous bone material. The external washer threads are tapered. The bone screw is inserted through the central bore of the washer and threaded into the fragment beyond the fracture. The washer permits the bone screw head to be located beneath the bone surface.

(6) United States Patent Application Publication Number 2010/0331895 to Linke.

United States Patent Application Publication Number 2010/0331895—published to Linke on Dec. 30, 2010 in U.S. class 606 and subclass 304—teaches an osteosynthetic device for the fixation of a bone or bone fragments, which has a longitudinal axis, and includes a bone screw with a shaft bearing a thread, a front end, and a rear end. The thread has a maximum outer diameter, and a wing-like blade with a leading end being connected to the front end of the bone screw and a trailing end being connected to the rear end of the bone screw. The blade is further provided with a coaxial longitudinal aperture having a length extending between the leading end and the trailing end, and a width. Further, the blade is coaxially and rotatably mounted on the shaft of the bone screw.

(7) United States Patent Application Publication Number 2010/0312245 to Tipirneni et al.

United States Patent Application Publication Number 2010/0312245—published to Tipirneni et al. on Dec. 9, 2010 in U.S. class 606 and subclass 62—teaches a bone screw including a sleeve, a shaft reciprocally received within the sleeve, and a compressive device. The bone screw may be extended—placing a fracture in tension—after insertion into a bone, and then retained in place by a setscrew that is retained by an intramedullary rod. The shaft of the bone screw has a blade thread that allows the bone screw to be installed into a bone by tapping the bone screw with a hammer.

It is apparent that numerous innovations for osteosynthetic devices have been provided in the prior art, which are adapted to be used. Furthermore, even though these innovations may be suitable for the specific individual purposes to which they address, nevertheless, they would not be suitable for the purposes of the embodiments of the present invention as heretofore described, namely, an interchangeable orthopedic blade for more accurately placing in, without excessive damage to, a bone when repairing a fracture in the bone by cooperating with an interchangeable orthopedic plate, so as to provide absolute stable fixation by holding the fracture in its anatomic position and resist applied forces while healing, to thereby provide a stable anatomic restoration and eliminate a need for revision surgery due to failure of fixation or malunion.

3. SUMMARY OF THE INVENTION

Thus, an object of the embodiments of the present invention is to provide an interchangeable orthopedic blade for more accurately placing in, without excessive damage to, a bone when repairing a fracture in the bone so as to provide absolute stable fixation by holding the fracture in its anatomic position and resist applied forces while healing, to thereby provide a stable anatomic restoration and eliminate a need for revision surgery due to failure of fixation or malunion, and for cooperating with an applicable interchangeable plate, which avoids the disadvantages of the prior art.

Briefly stated, another object of the embodiments of the present invention is to provide an interchangeable orthopedic blade that more accurately places in, without excessive damage to, a bone when repairing a fracture in the bone so as to provide absolute stable fixation by holding the fracture in its anatomic position and resist applied forces while healing, to thereby provide a stable anatomic restoration and eliminate a need for revision surgery due to failure of fixation or malunion, and further cooperating with an applicable interchangeable plate. The interchangeable orthopedic blade includes an internal portion and an external portion. The internal portion more accurately places the interchangeable orthopedic blade in, without excessive damage to, the bone when repairing the fracture in the bone and ultimately provide absolute stable fixation by the interchangeable orthopedic blade holding the fracture in its anatomic position and resisting applied forces while healing, to thereby provide a stable anatomic restoration and eliminate a need for revision surgery due to failure of fixation or malunion. The internal portion is received in the external portion and rotates relative to the external portion, but has the external portion move non-rotatably axially with the internal portion into the bone as the internal portion threads. In a first preferred embodiment, the internal portion is a screw with an externally threaded head. In a second preferred embodiment, the internal portion is an externally threaded set screw.

The novel features considered characteristic of the embodiments of the present invention are set forth in the appended claims. The embodiments of the present invention themselves, however, both as to their construction and to their method of operation together with additional objects and advantages thereof will be best understood from the following description of the embodiments of the present invention when read and understood in connection with the accompanying figures of the drawing.

4. BRIEF DESCRIPTION OF THE FIGURES OF THE DRAWING

The figures of the drawing are briefly described as follows:

FIG. 8 is a diagrammatic side plan views of a T-lag screw compressing a clean fracture;

FIG. 9 is a diagrammatic side elevational view of a T-lag screw compressing a jagged fracture;

FIG. 15 is a diagrammatic side elevational view of the application of the drill guides depending on the proposed function of the screw through a neutral position and a compression position;

Figure 1:
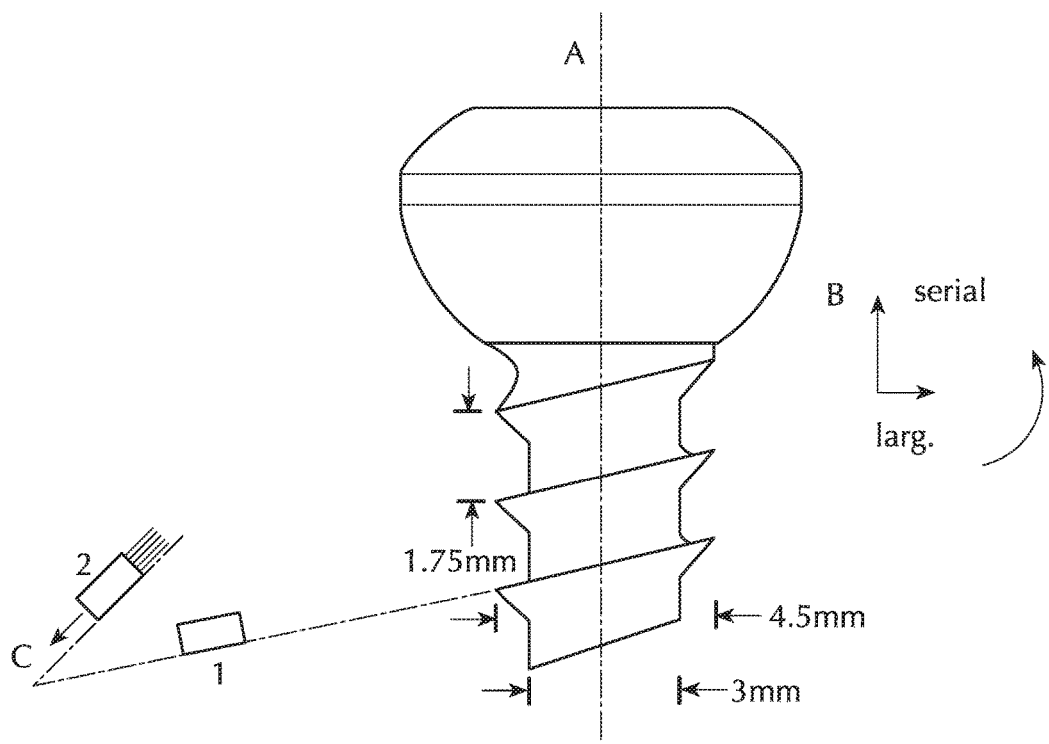
FIG. 1 is a diagrammatic side elevational view of a common screw.
Figure 2:
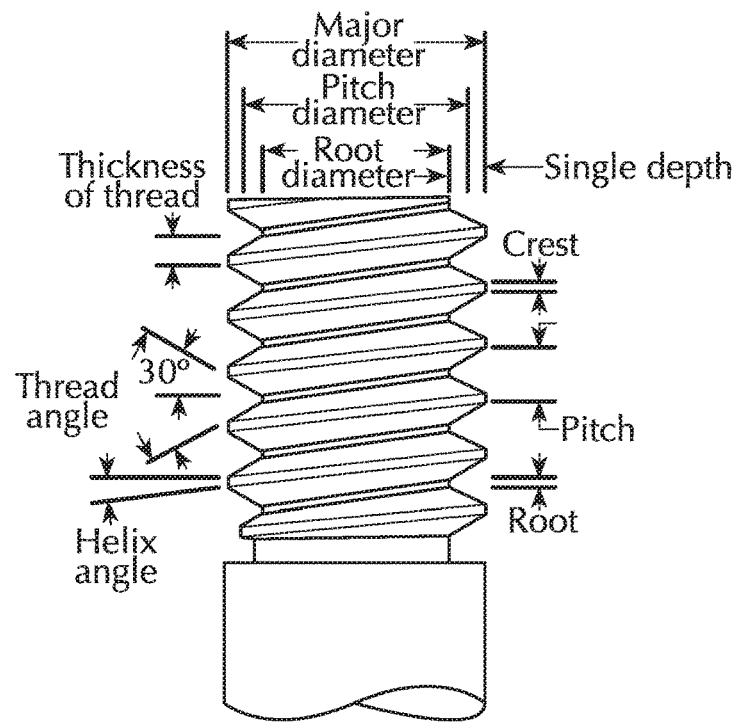
FIG. 2 is a diagrammatic side elevational view of the threads of a common screw, which are defined by its major or outside and minor or root diameters, pitch, lead, and number of threads.
Figure 3:
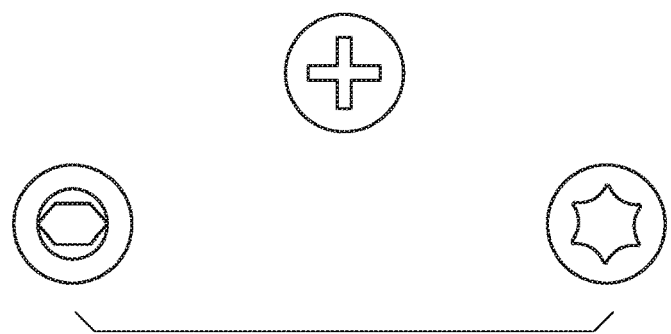
FIG. 3 is a diagrammatic top plan view of the head drive types of the common screw.
Figure 4:
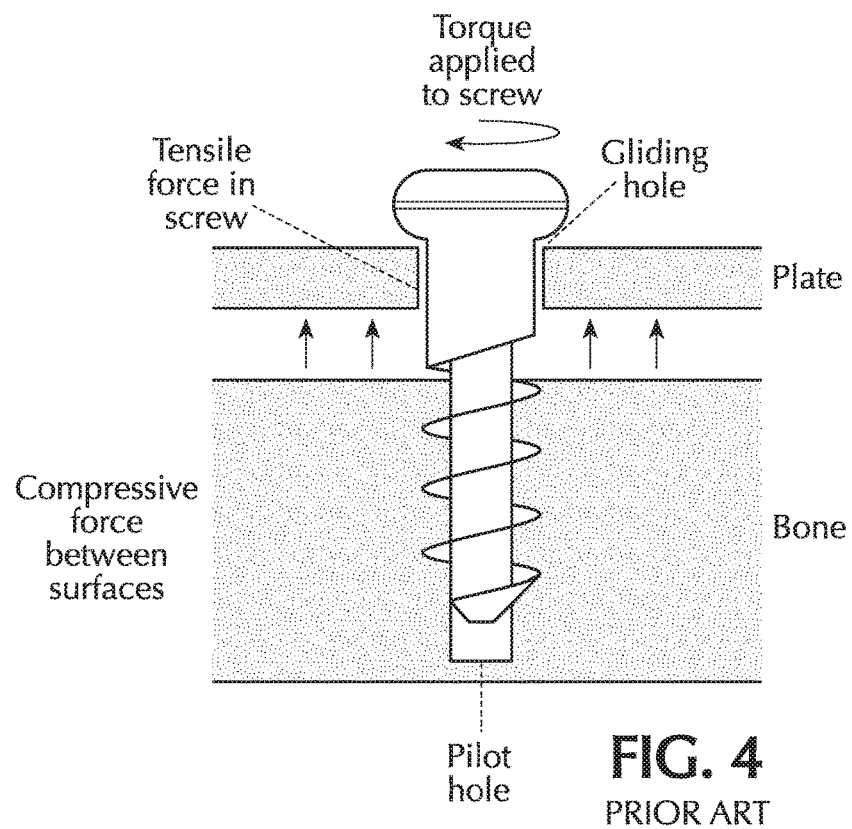
FIG. 4 is a diagrammatic side elevational view of the biomechanics of cannulated and noncannulated screws.
Figure 5:
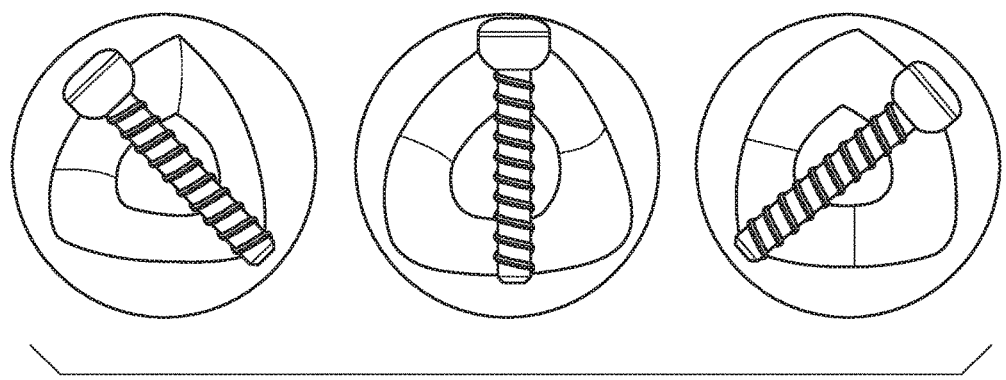
FIG. 5 is a diagrammatic top plan view of lag screw fixation that produces maximum interfragmentary compression when the screw is placed perpendicular to the fracture line.
Figure 6:
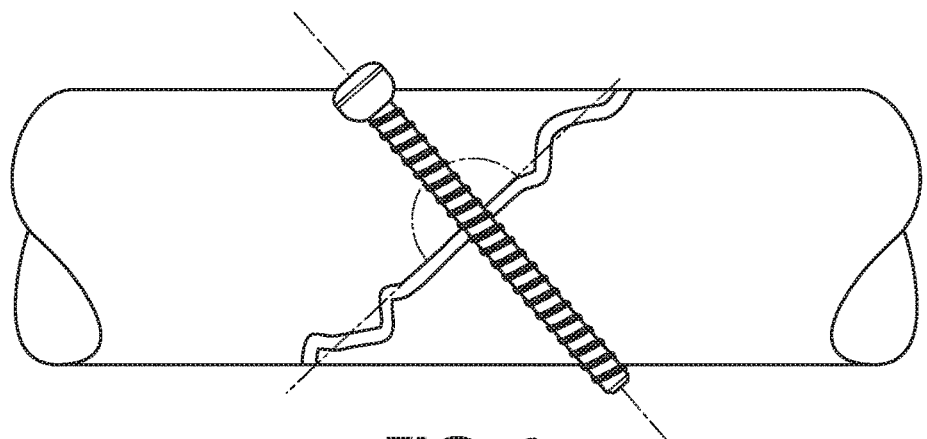
FIG. 6 is a diagrammatic side elevational view showing lag screw fixation producing maximum interfragmentary compression when the screw is placed perpendicular to the fracture line.
Figure 7:
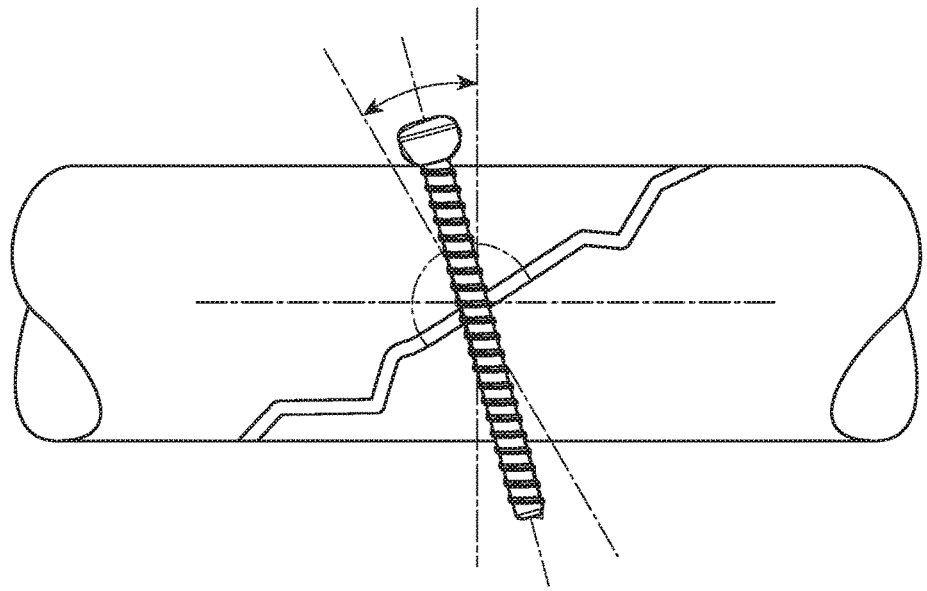
FIG. 7 is a diagrammatic side elevational view showing lag screw fixation producing minimum interfragmentary compression when the screw is not placed perpendicular to the fracture line.
Figure 10:
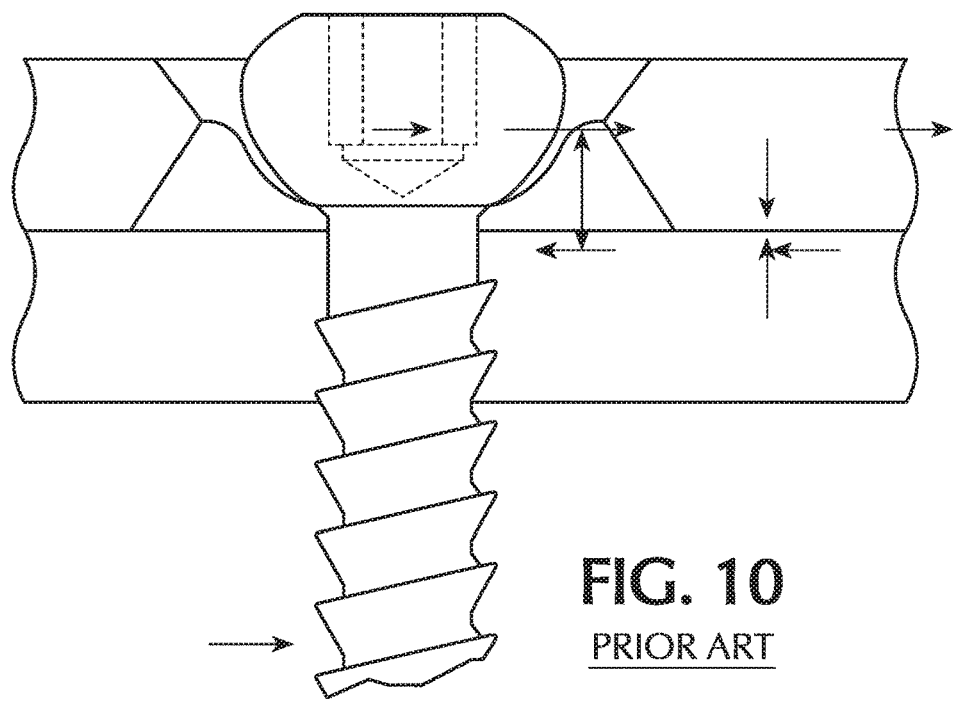
FIG. 10 is a diagrammatic side elevational view of a locked plate screw functioning as a bolt.
Figure 11:
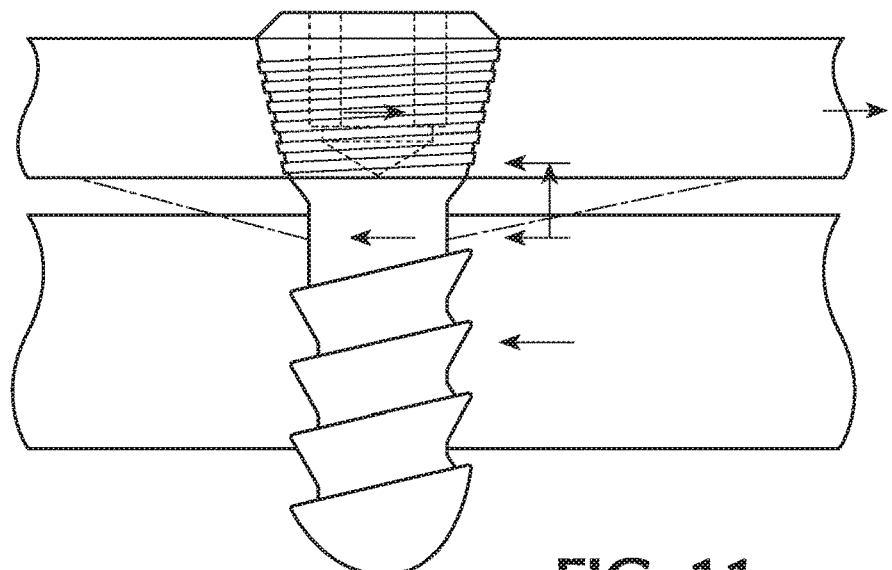
FIG. 11 is a diagrammatic side elevational view of another locked plate screw functioning as an internal-external fixator.
Figure 12:
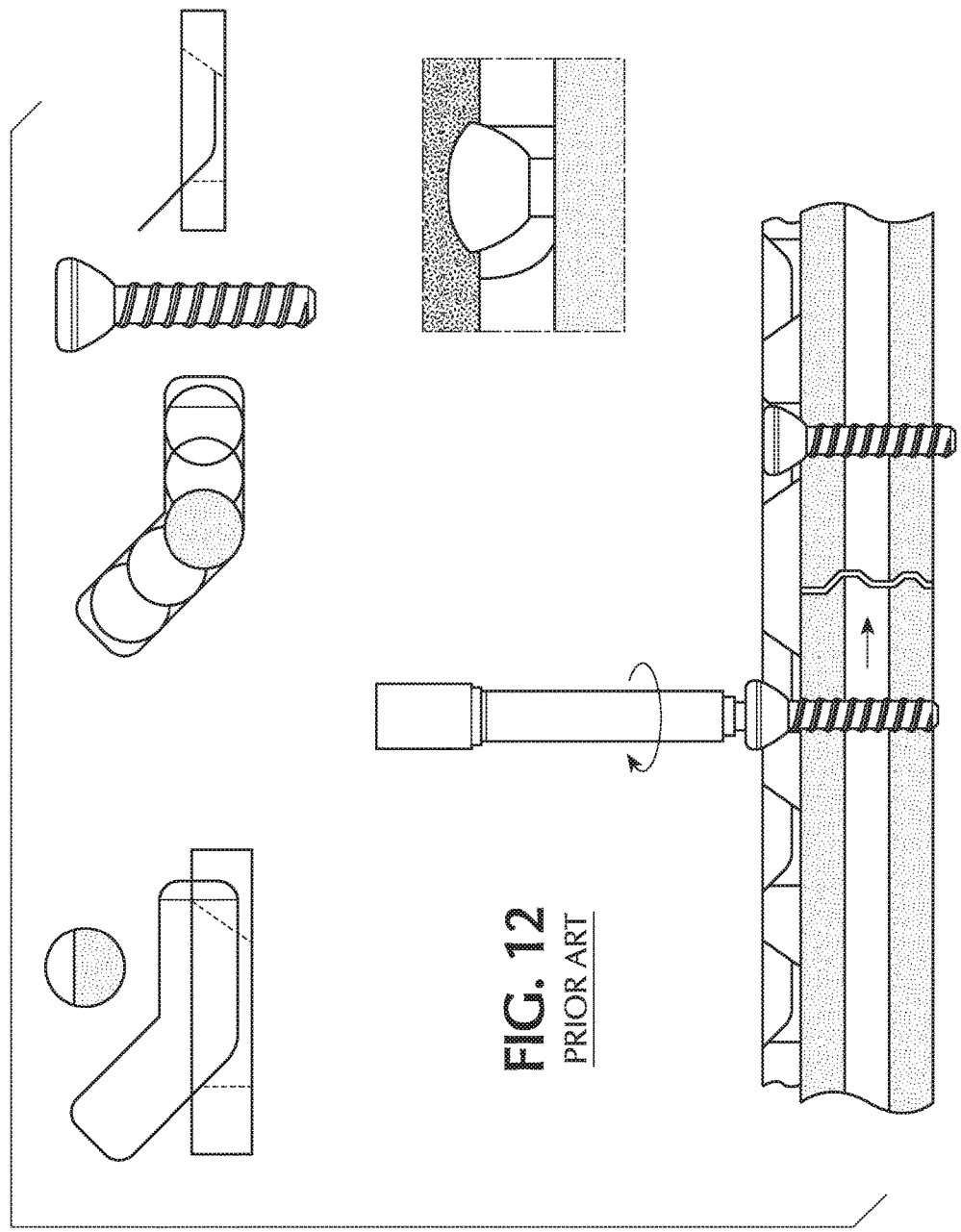
FIG. 12 is a diagrammatic side elevational view illustrating the dynamic compression principle.
Figure 13:
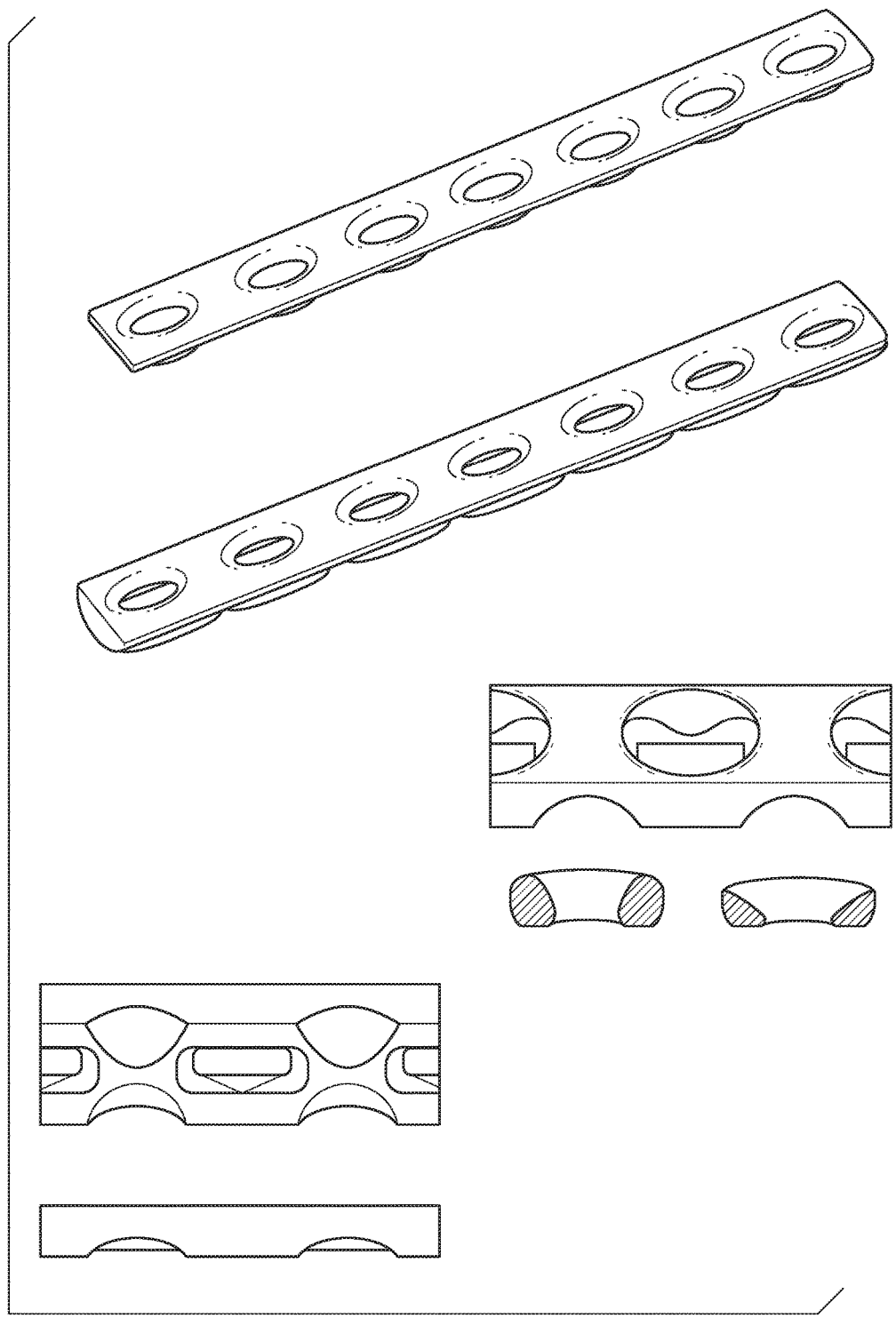
FIG. 13 is diagrammatic side elevational view of the structure of a limited-contact dynamic compression plate.
Figure 14A:
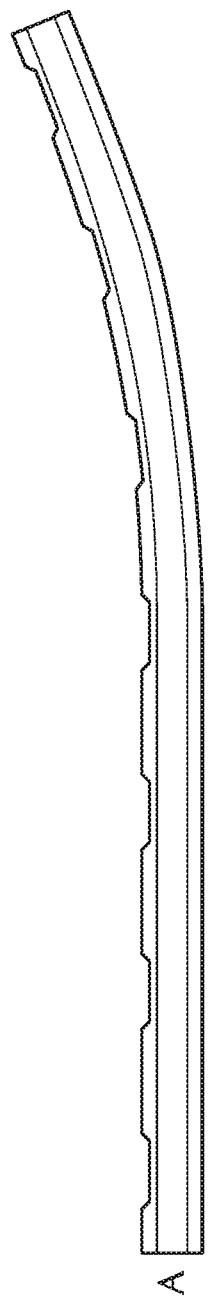
FIG. 14A is a diagrammatic side elevational view illustrating that in the dynamic compression plate, the area at the plate holes is less stiff than the area between them so that during bending, the plate tends to bend only in the areas of the holes.
Figure 14B:
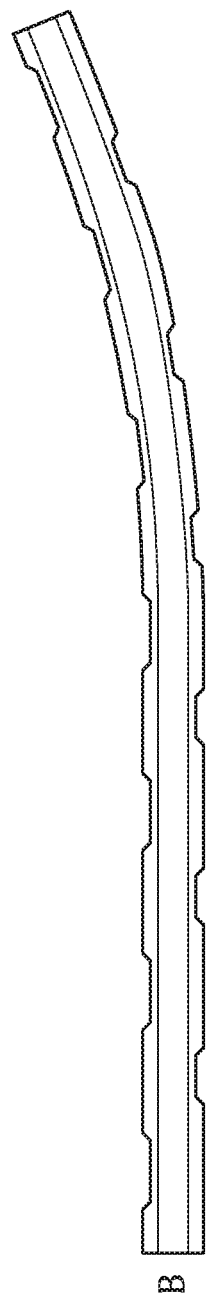
FIG. 14B is a diagrammatic side elevational view of the limited-contact dynamic compression plate having an even stiffness without the risk of buckling at the screw holes.
Figure 16:
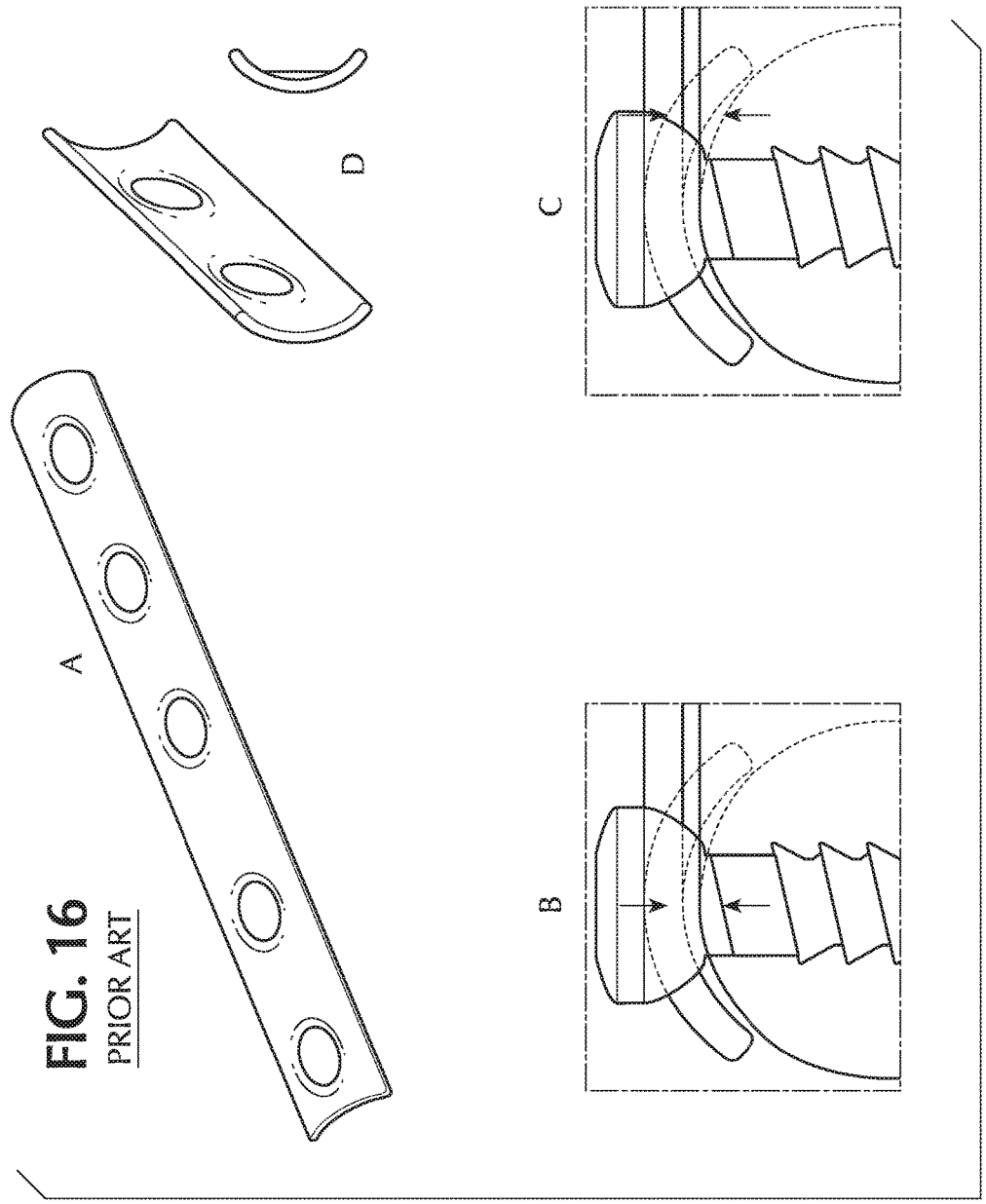
FIG. 16 is a diagrammatic elevational view of the 3.5 one-third tubular plate that is 1 mm thick and allows for limited stability so that the thin design allows for easy shaping and is primarily used on the lateral malleolus and distal ulna, wherein the oval holes allow for limited fracture compression with eccentric screw placement.
Figure 17B:
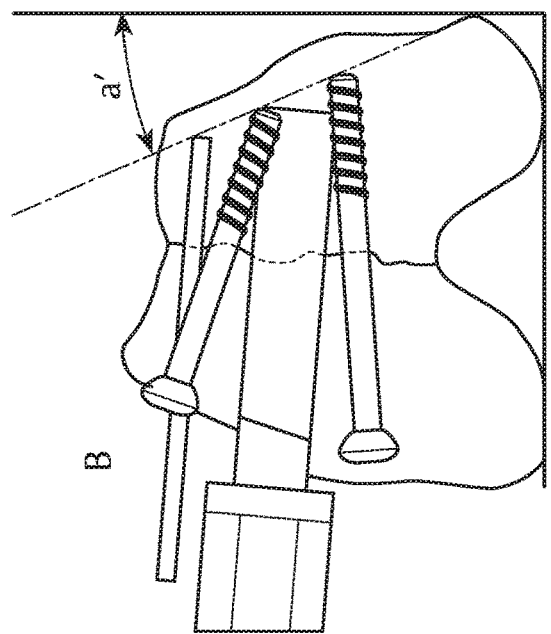
Figure 17A:
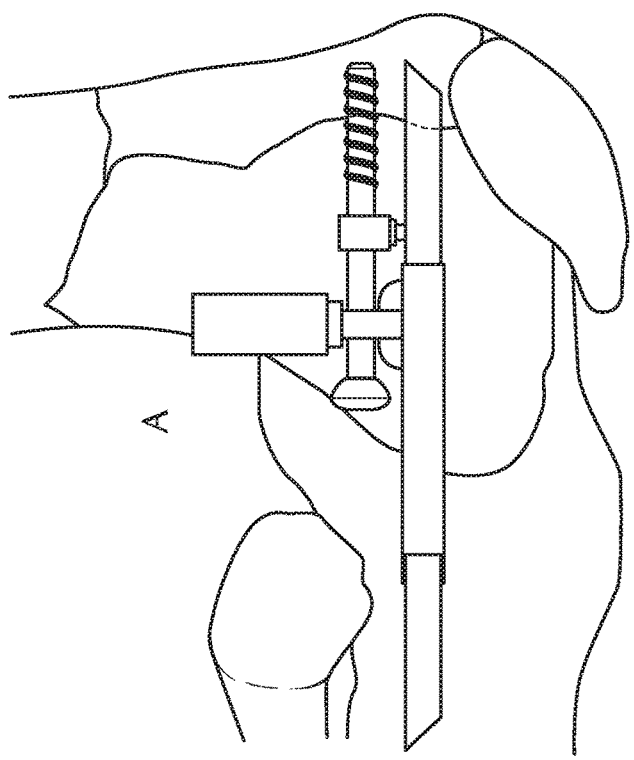
Figure 17D:
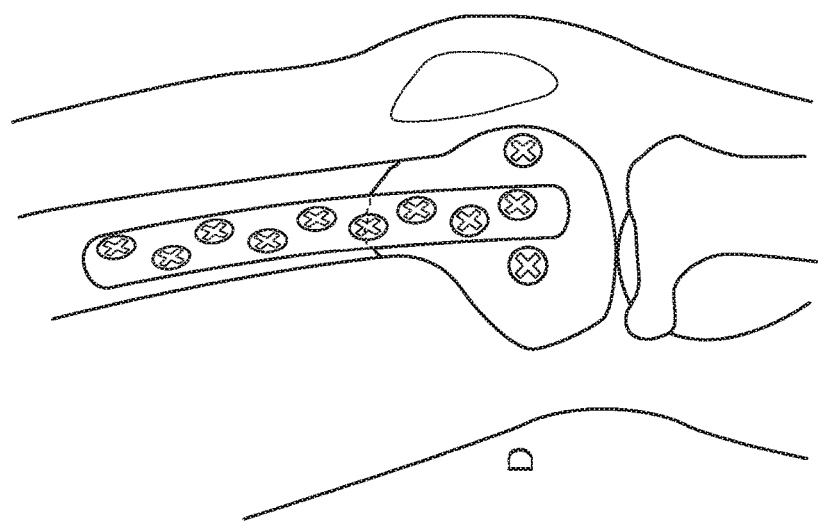
Figure 17C:
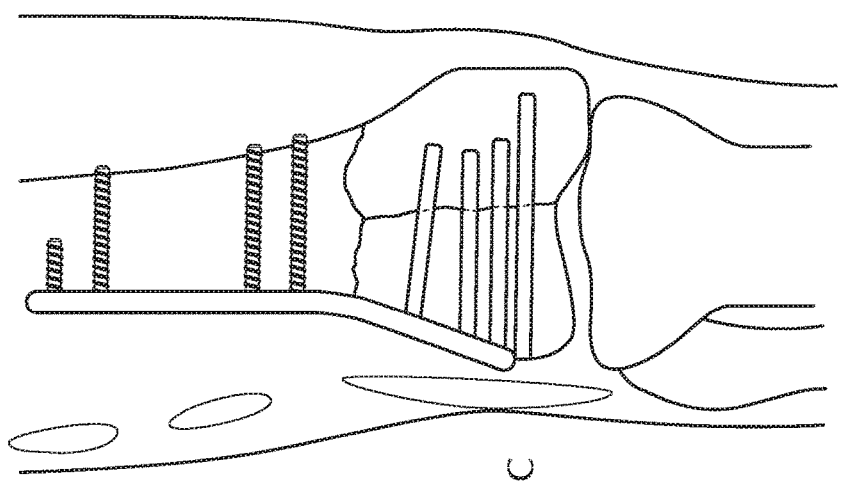
Figure 18A:
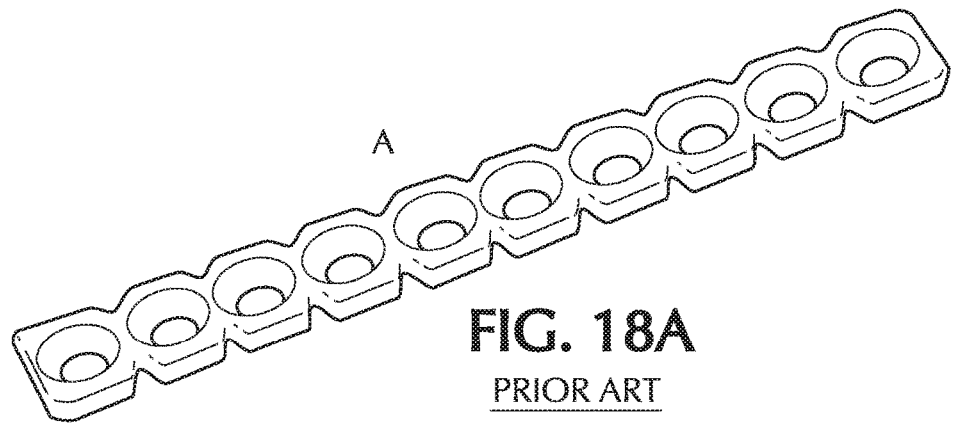
Figure 18B:
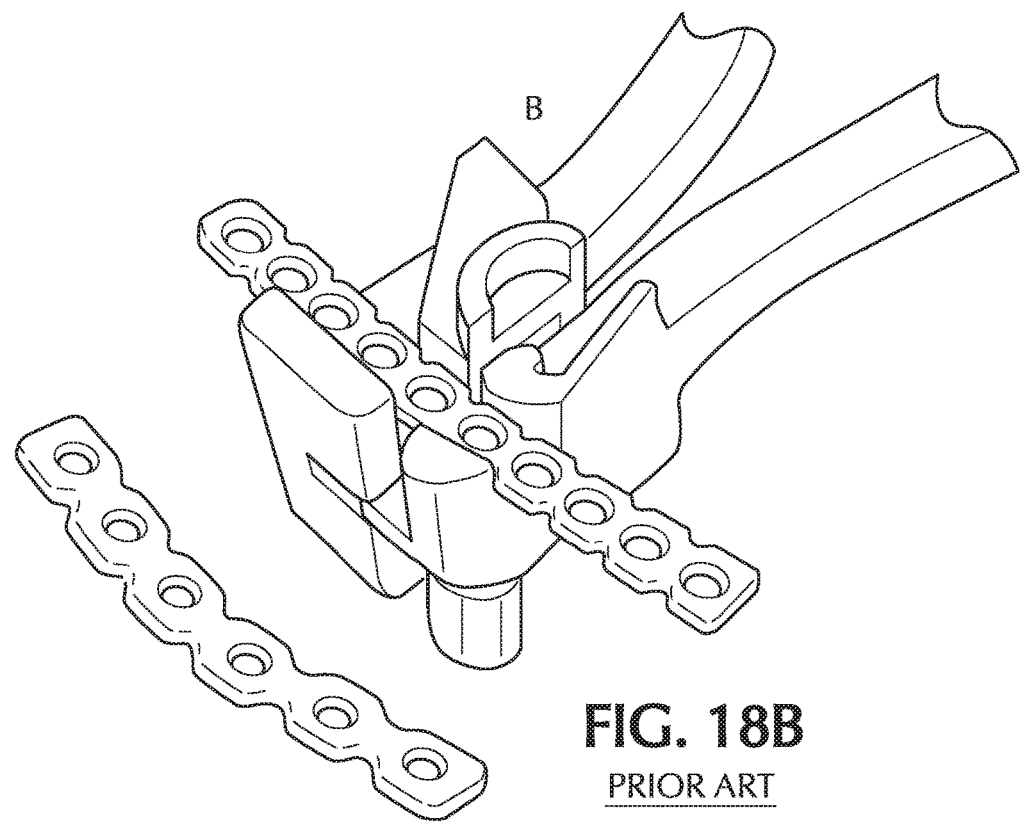
Figure 19B:
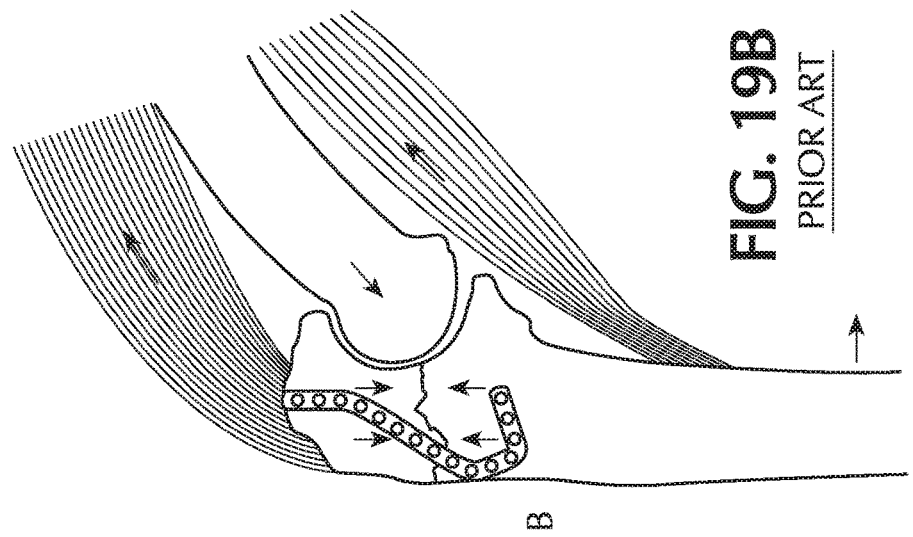
Figure 19A:
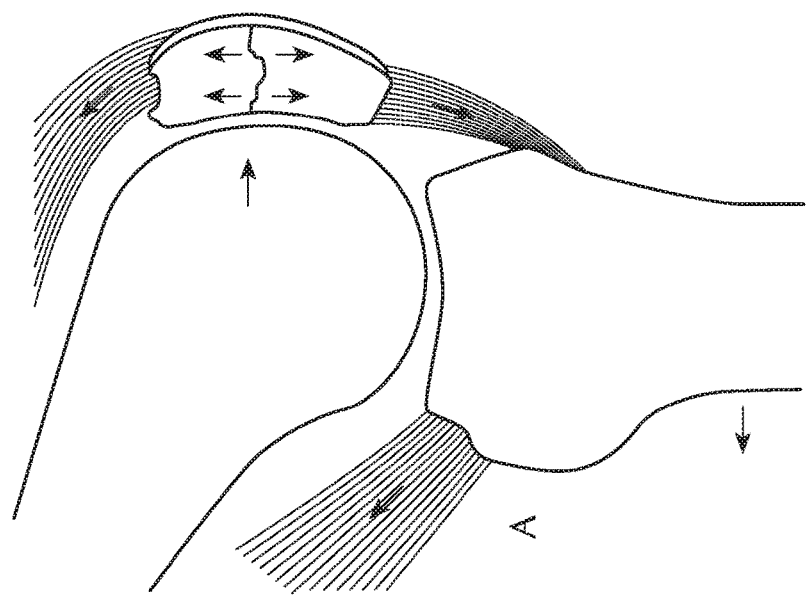
Figure 20:
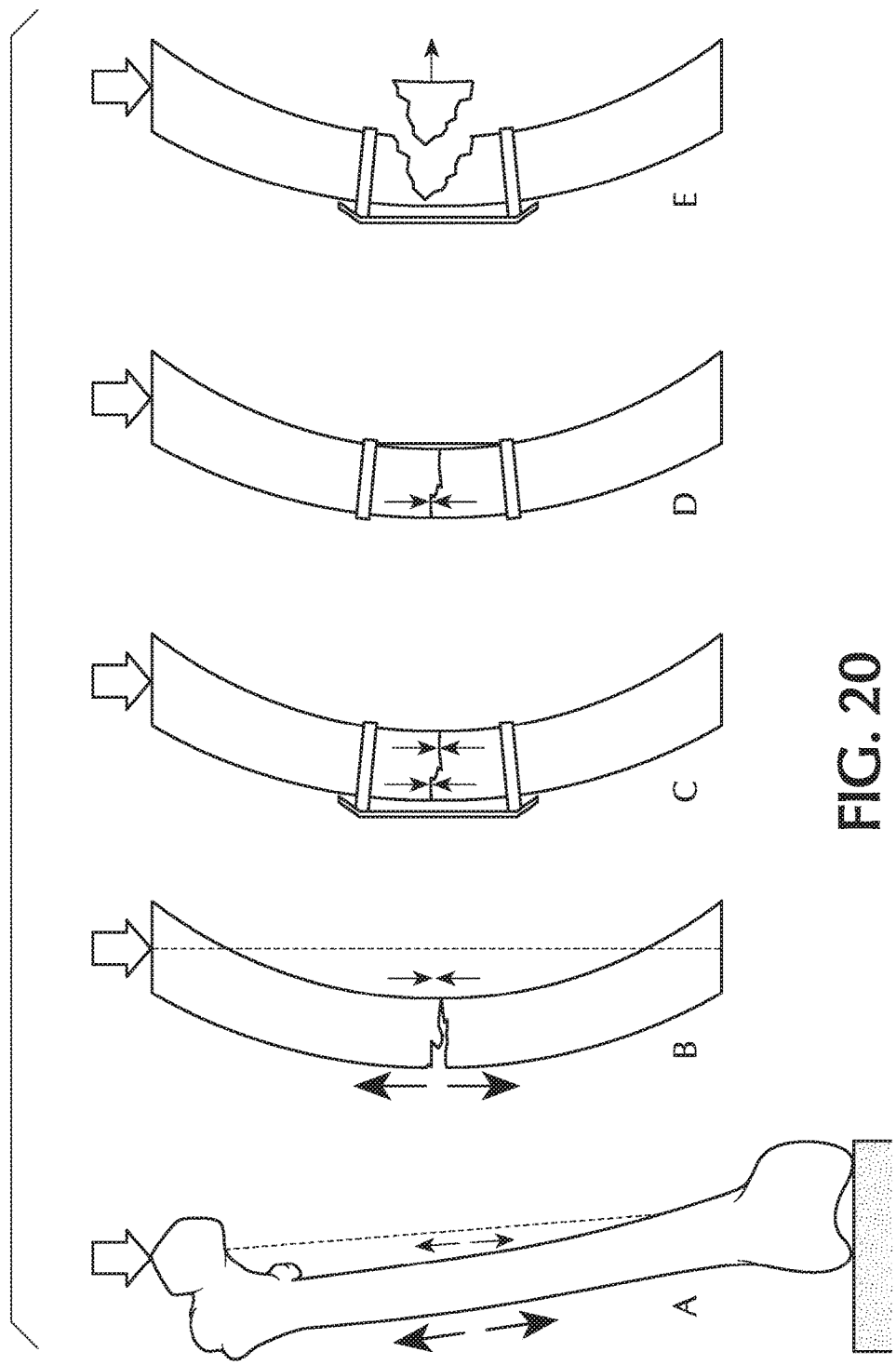
Figure 21:
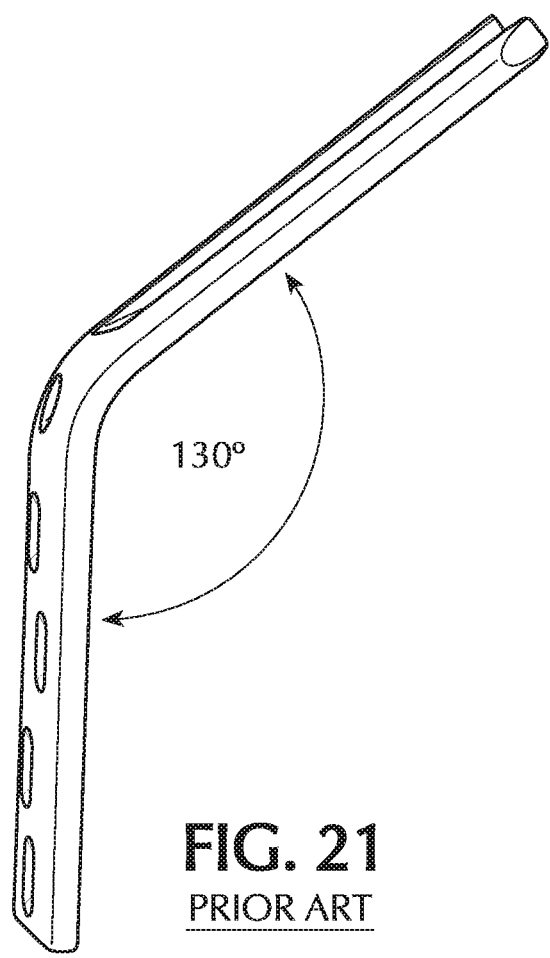
Figure 22:
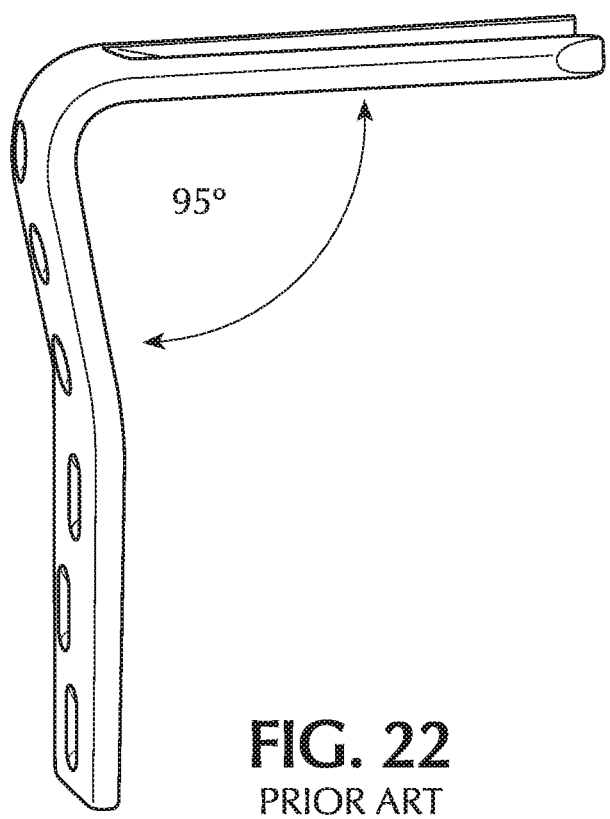
Figure 23:
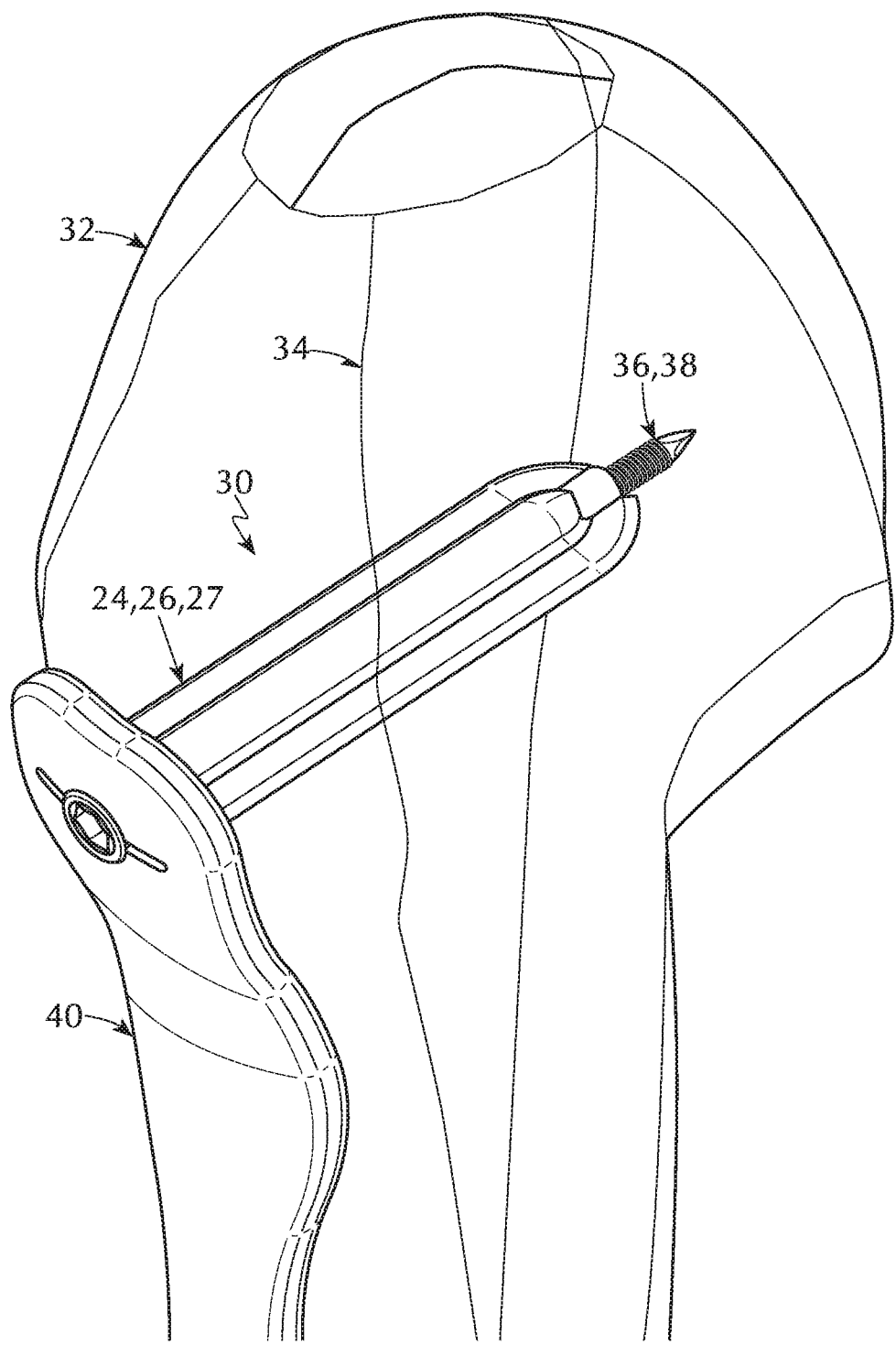
Figure 24:
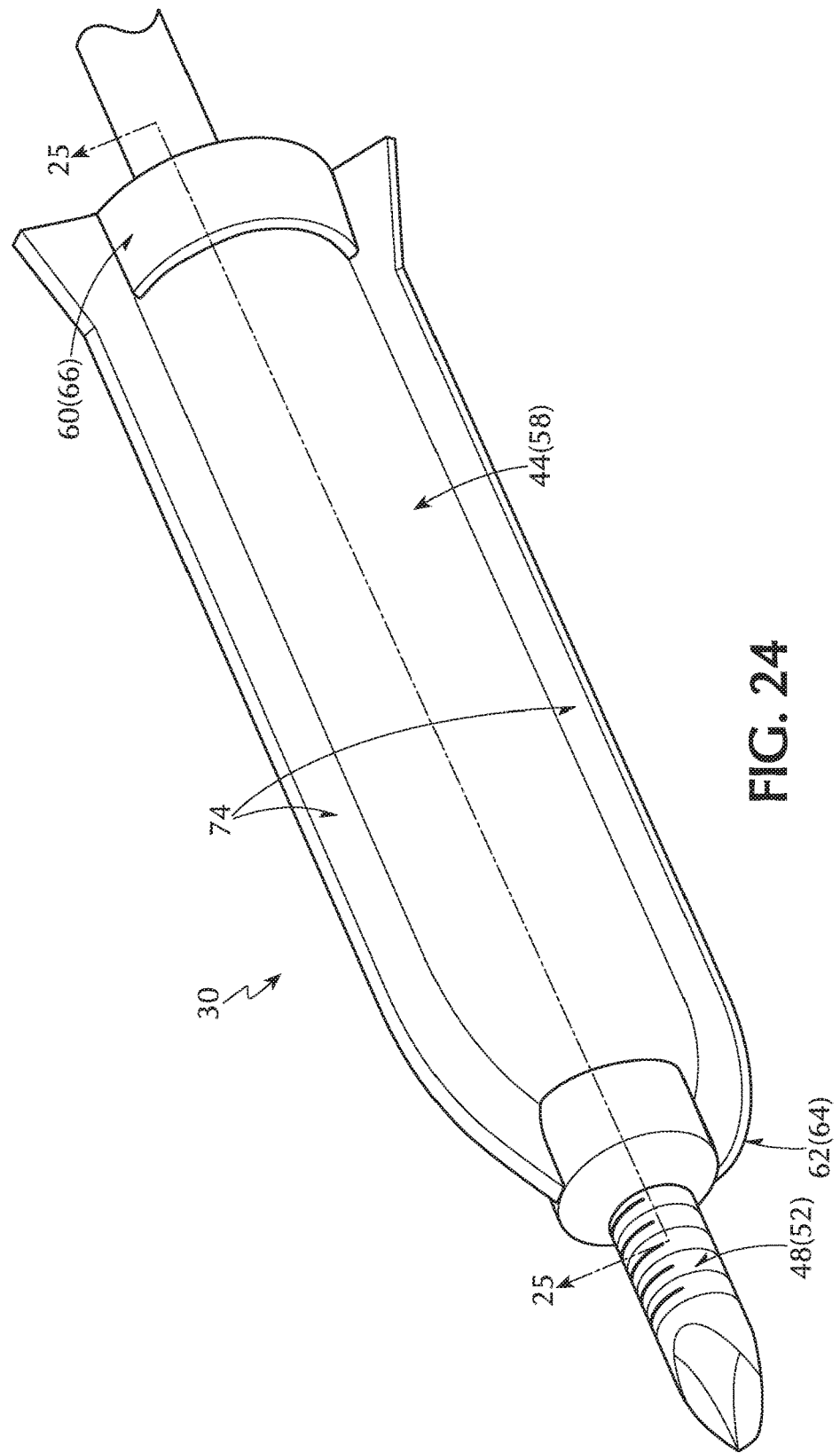
Figure 25:
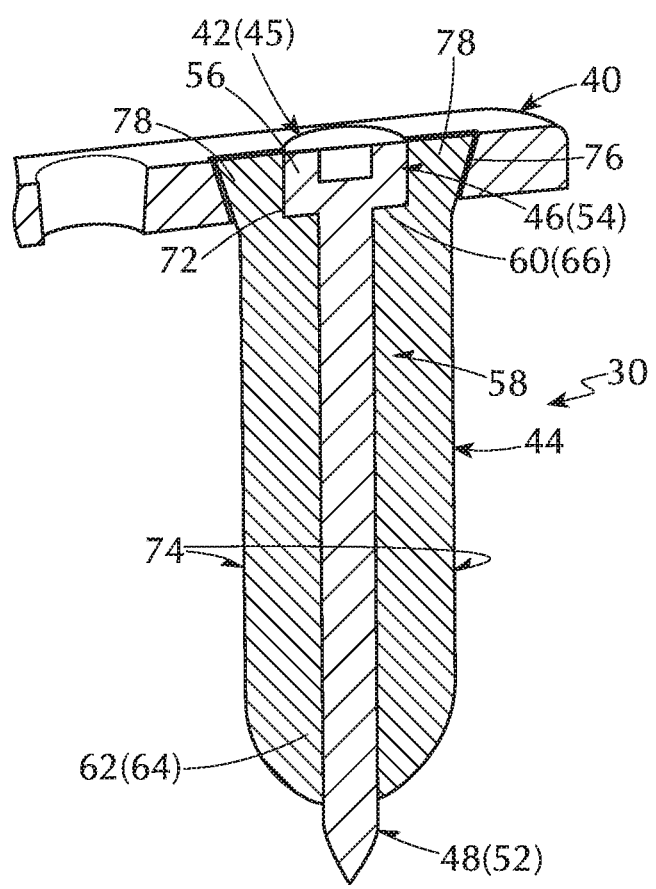
Figure 27:
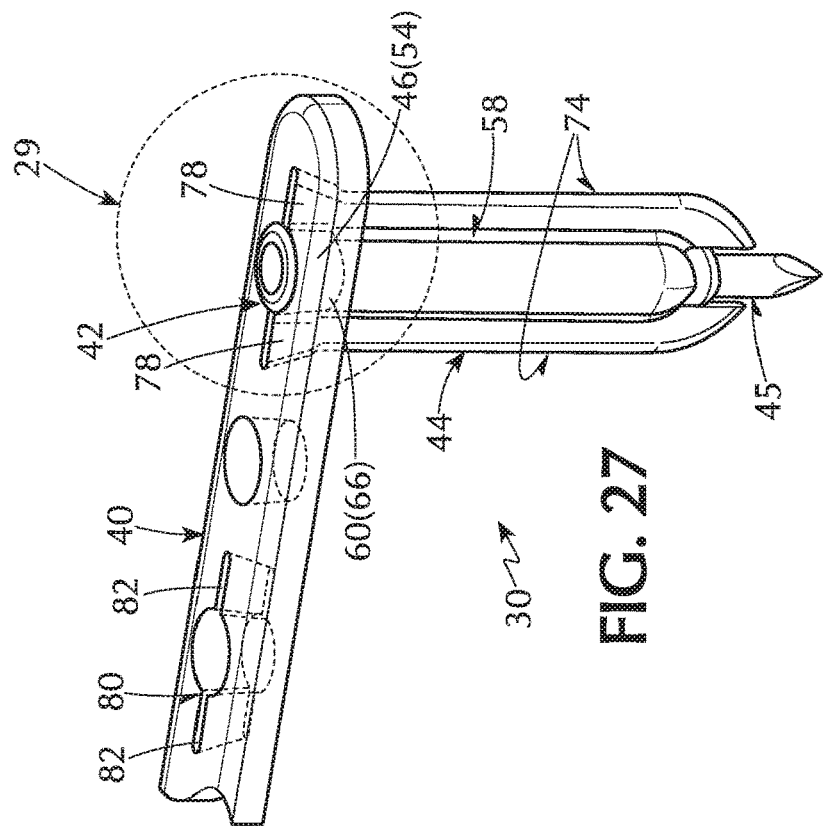
Figure 26:
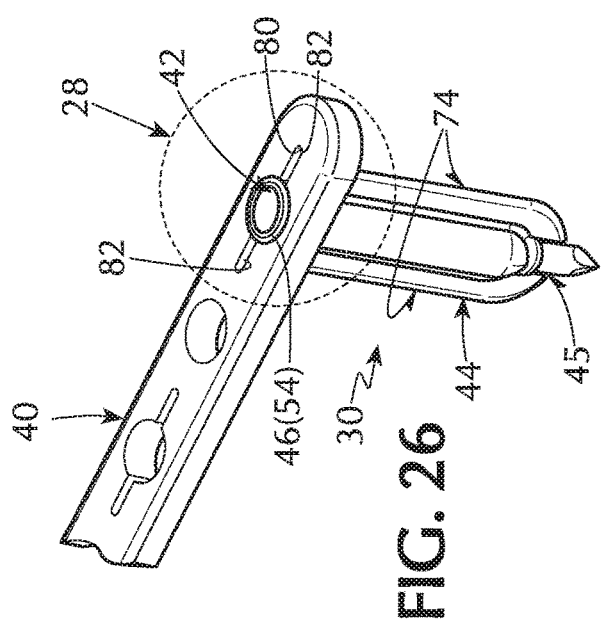
Figure 28:
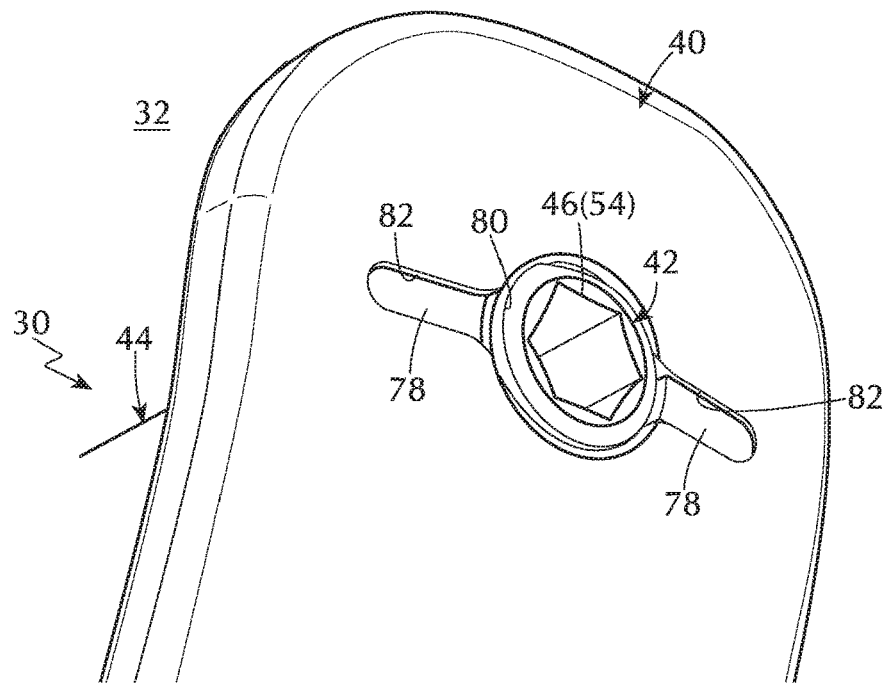
Figure 29:
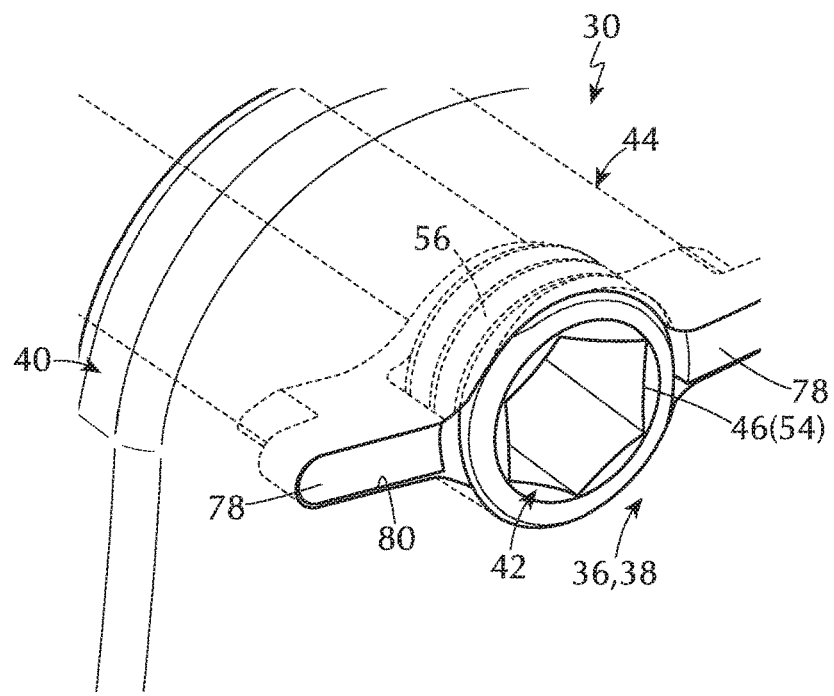
Figure 30:
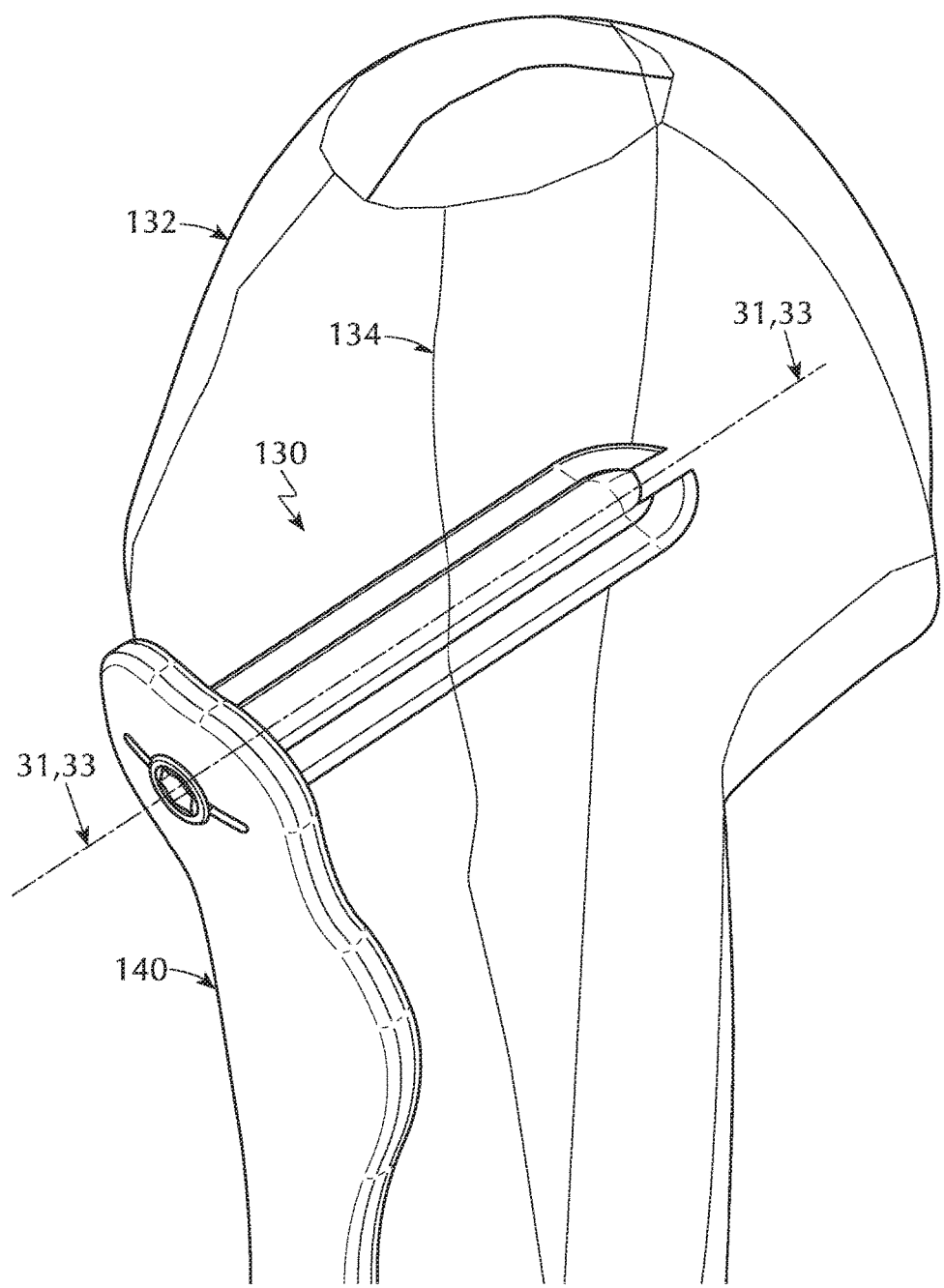
Figure 31:
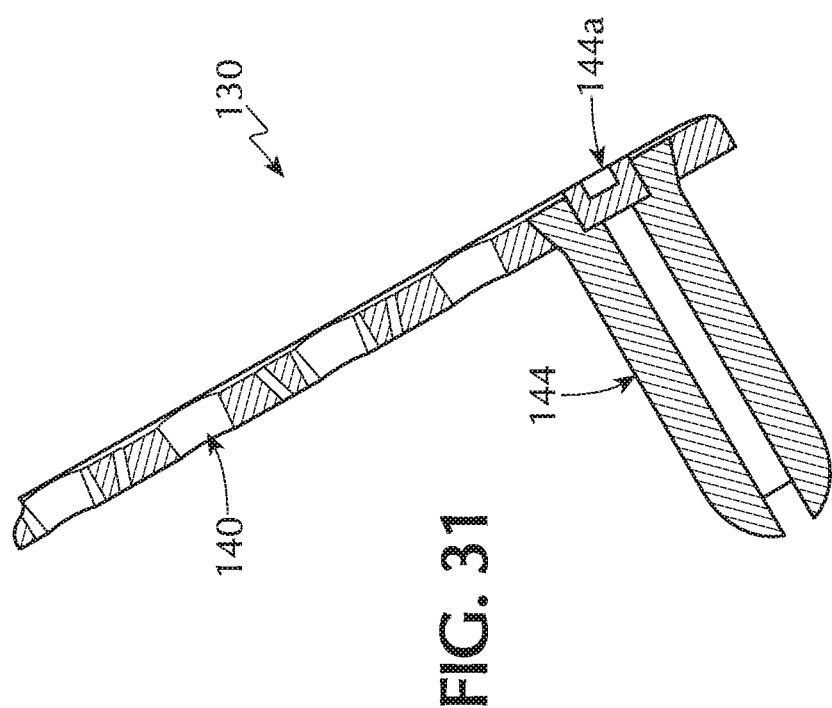
Figure 32:
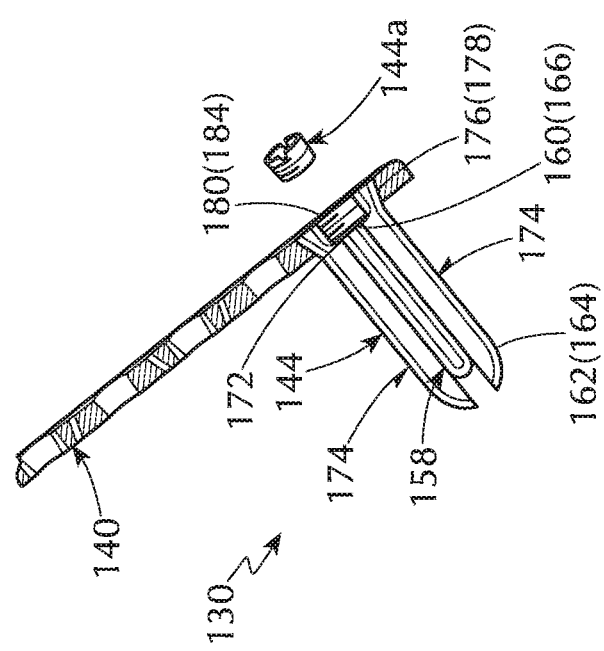
Figure 33:
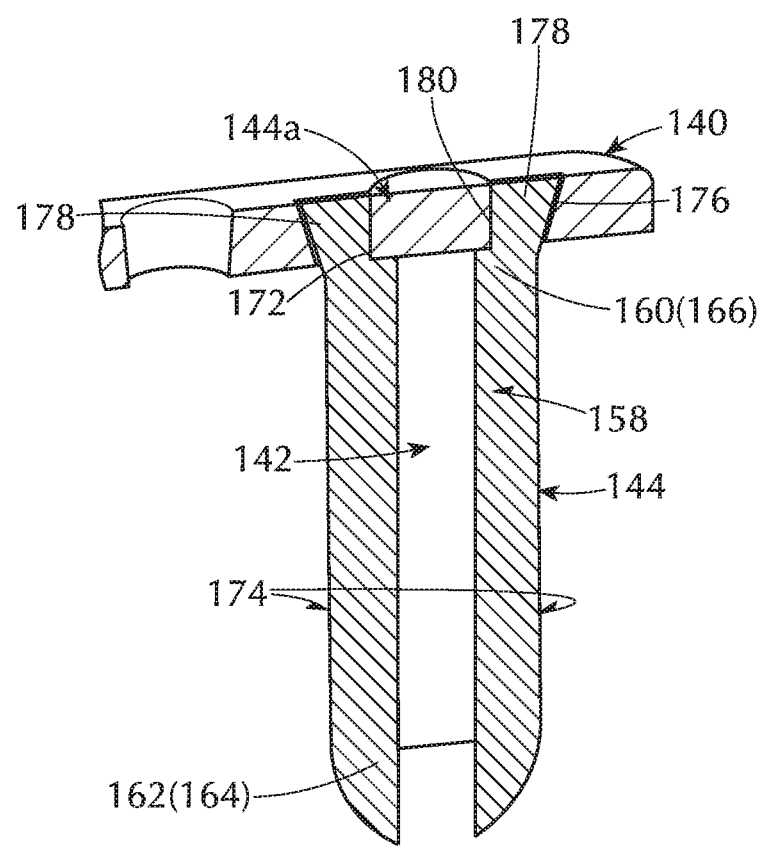

FIGS. 17A-17D are diagrammatic side elevational views of angled or blade plates that are useful in repair of metaphyseal fractures of the femur, but the popularity has declined with the rise of sliding screw plates and locking plates, wherein proper insertion requires careful technique, with the blade inserted with consideration for 3 dimensions (varus/valgus blade angulation, anterior/posterior blade position, and flexion/extension rotation of blade plate);

FIGS. 18A and 18B are diagrammatic perspective views of reconstruction plates that are thicker than the tubular plates but not quite as thick as dynamic compression plates, and designed with deep notices between the holes, and can be contoured in 3 planes to fit complex surfaces, as around the pelvis and acetabulum, wherein reconstruction plates are provided in straight and slightly thicker and stiffer precurved lengths, and wherein as with tubular plates, they have oval screw holes allowing potential for limited compression;

FIGS. 19A and 19B are diagrammatic side elevational views illustrating the tension-band principle;

FIG. 20 is diagrammatic side elevational view illustrating the tension-band principle at the femur;

FIG. 21 is a diagrammatic perspective view of an angled plate;

FIG. 22 is a diagrammatic perspective view of another type of angled plate;

FIG. 23 is a diagrammatic perspective view of the first embodiment of the interchangeable orthopedic blade of the embodiments of the present invention more accurately placing in, without excessive damage to, a bone when repairing a fracture in the bone so as to provide absolute stable fixation by holding the fracture in its anatomic position and resist applied forces while healing, to thereby provide a stable anatomic restoration and eliminate a need for revision surgery due to failure of fixation or malunion, and for cooperating with an applicable interchangeable plate;

FIG. 24 is an enlarged diagrammatic perspective view of the interchangeable orthopedic blade of the embodiments of the present invention identified by ARROW 24 in FIG. 23;

FIG. 25 is a reduced diagrammatic cross sectional view taken along LINE 25-25 in FIG. 24;

FIG. 26 is a diagrammatic perspective view of the interchangeable orthopedic blade of the embodiments of the present invention cooperating with an applicable interchangeable plate identified by ARROW 26 in FIG. 23;

FIG. 27 is a diagrammatic perspective view of the interchangeable orthopedic blade of the embodiments of the present invention cooperating with an applicable interchangeable plate identified by ARROW 27 in FIG. 23;

FIG. 28 is an enlarged diagrammatic perspective view of the area generally enclosed by the dotted curve identified by ARROW 28 in FIG. 26;

FIG. 29 is an enlarged diagrammatic perspective view of the area generally enclosed by the dotted curve identified by ARROW 29 in FIG. 27;

FIG. 30 a diagrammatic perspective view of the second embodiment of the interchangeable orthopedic blade of the embodiments of the present invention more accurately placing in, without excessive damage to, a bone when repairing a fracture in the bone so as to provide absolute stable fixation by holding the fracture in its anatomic position and resist applied forces while healing, to thereby provide a stable anatomic restoration and eliminate a need for revision surgery due to failure of fixation or malunion, and for further cooperating with an applicable interchangeable plate;

FIG. 31 is a cross sectional view of the interchangeable orthopedic blade of the embodiments of the present invention taken along LINE 31-31 in FIG. 30;

FIG. 32 is an exploded diagrammatic side elevational view of the interchangeable orthopedic blade identified by ARROW 32 in FIG. 30; and FIG. 33 is a cross sectional view of the interchangeable orthopedic blade of the embodiments of the present invention taken along LINE 33-33 in FIG. 30.

5. LIST OF REFERENCE NUMERALS UTILIZED IN THE FIGURES OF THE DRAWING

A. Introductory—First Embodiment

30 interchangeable orthopedic blade of embodiments of present invention for more accurately placing in, without excessive damage to, bone 32 when repairing fracture 34 in bone 32 so as to provide absolute stable fixation by holding fracture 34 in anatomic position and resist applied forces while healing, to thereby provide stable anatomic restoration and eliminate need for revision surgery due to failure of fixation or malunion, and for further cooperating with applicable interchangeable plate 40

32 bone

34 fracture of bone 32

40 applicable interchangeable plate

B. Overall Configuration of First Embodiment of Interchangeable Orthopedic Blade 30

42 internal portion for more accurately placing interchangeable orthopedic blade 30 in, without excessive damage to, bone 32 when repairing fracture 34 in bone 32 and ultimately provide absolute stable fixation by interchangeable orthopedic blade 30 holding fracture 34 in anatomic position and resisting applied forces while healing, to thereby provide stable anatomic restoration and eliminate need for revision surgery due to failure of fixation or malunion

44 external portion

C. Specific Configuration of Internal Portion 42 and External Portion 44

(1) Internal Portion 42.

45 slender and elongated screw of internal portion 42

46 proximal end of slender and elongated screw 45 of internal portion 42

48 distal end of slender and elongated screw 45 of internal portion 42

50 external threads of slender and elongated screw 45 of internal portion 42 for threadably engaging into bone 32

52 tapered distal end of distal end 48 of slender and elongated screw 45 of internal portion 42 for facilitating passage through bone 32

54 screw head of proximal end 46 of slender and elongated screw 45 of internal portion 42 for threadably engaging in applicable interchangeable plate 40

56 external threads of screw head 54 of proximal end 46 of slender and elongated screw 45 of internal portion 42

(2) External Portion 44.
58 slender, elongated, and generally cylindrically shaped sleeve of external portion 44
60 proximal end of slender, elongated, and generally cylindrically shaped sleeve 58 of external portion 44
62 distal end of slender, elongated, and generally cylindrically shaped sleeve 58 of external portion 44
64 tapered and/or fluted distal end of distal end 62 of slender, elongated, and generally cylindrically shaped sleeve 58 of external portion 44 for facilitating passage through bone 32 during threading of slender and elongated screw 45 of internal portion 42 into bone 32
66 ring-like proximal end of proximal end 60 of slender, elongated, and generally cylindrically shaped sleeve 58 of external portion 44
72 at least a shoulder defining ring-like proximal end 66 of proximal end 60 of slender, elongated, and generally cylindrically shaped sleeve 58 of external portion 44
74 at least one fin of external portion 44
76 portion of at least one fin 74 of external portion 44
78 at least one diverging fin extension of at least one fin 74 of external portion 44

D. Method of Utilizing Interchangeable Orthopedic Blade 30 in Cooperation with Applicable Interchangeable Plate 40

80 specifically configured through bore in applicable interchangeable plate 40
82 at least one tapered cutout of specifically configured through bore 80 in applicable interchangeable plate 40
84 threads in specifically configured through bore 80 in applicable interchangeable plate 40

E. Introductory—Second Embodiment 130 interchangeable orthopedic blade of embodiments of present invention for more accurately placing in, without excessive damage to, bone 132 when repairing fracture 134 in bone 132 so as to provide absolute stable fixation by holding fracture 134 in anatomic position and resist applied forces while healing, to thereby provide stable anatomic restoration and eliminate need for revision surgery due to failure of fixation or malunion, and for further cooperating with applicable interchangeable plate 140
132 bone
134 fracture in bone 132
140 applicable interchangeable plate F. Overall Configuration of Second Embodiment of Interchangeable Orthopedic Blade 130

142 internal portion
144 external portion

G. Specific Configuration of Internal Portion 142 and External Portion 144

(1) Internal Portion 142.
144a fastener of internal portion 142
144c externally threaded set screw of fastener 144a of internal portion 142
(2) External Portion 144.
158 slender, elongated, and generally cylindrically shaped sleeve of external portion 144
160 proximal end of slender, elongated, and generally cylindrically shaped sleeve 158 of external portion 144
162 distal end of slender, elongated, and generally cylindrically shaped sleeve 158 of external portion 144
164 tapered and/or fluted distal end of distal end 162 of slender, elongated, and generally cylindrically shaped sleeve 158 of external portion 144 for facilitating passage through bone 132
166 ring-like proximal end of proximal end 160 of slender, elongated, and generally cylindrically shaped sleeve 158 of external portion 144
172 shoulder of ring-like proximal end 166 of proximal end 160 of slender, elongated, and generally cylindrically shaped sleeve 158 of external portion 144
174 at least one fin of external portion 144
176 portion of at least one fin 174 of external portion 144
178 at least one diverging fin extension of at least one fin 174 of external portion 144
180 specifically configured through bore in applicable interchangeable plate 140
182 at least one tapered cutout of specifically configured through bore 180 in applicable interchangeable plate 140

H. Method of Utilizing Interchangeable Orthopedic Blade 130 in Cooperation with Applicable Interchangeable Plate 140

184 internal threads in specifically configured through bore 180 in applicable interchangeable plate 140

6. DETAILED DESCRIPTION OF THE PREFERRED EMBODIMENTS

A. Introductory—First Embodiment

Referring now to FIG. 23, the interchangeable orthopedic blade of the embodiments of the present invention is shown generally at 30 for more accurately placing in, without excessive damage to, a bone 32 when repairing a fracture 34 in the bone 32 so as to provide absolute stable fixation by holding the fracture 34 in its anatomic position and resist applied forces while healing, to thereby provide a stable anatomic restoration and eliminate a need for revision surgery due to failure of fixation or malunion, and for further cooperating with an applicable interchangeable plate 40.

B. Overall Configuration of the First Embodiment of the Interchangeable Orthopedic Blade 30

The overall configuration of the first embodiment of the interchangeable orthopedic blade 30 can best be seen in FIG. 24, and as such, will be discussed with reference thereto.

The interchangeable orthopedic blade 30 comprises an internal portion 42 and an external portion 44.

The internal portion 42 is for more accurately placing the interchangeable orthopedic blade 30 in, without excessive damage to, the bone 32 when repairing the fracture 34 in the bone 32 and ultimately provide absolute stable fixation by the interchangeable orthopedic blade 30 holding the fracture 34 in its anatomic position and resisting applied forces while healing, to thereby provide a stable anatomic restoration and eliminate a need for revision surgery due to failure of fixation or malunion. The internal portion 42 is received in the external portion 44. The internal portion 42 rotates relative to the external portion 44, but has the external portion 44 move non-rotatably axially with the internal portion 42 into the bone 32 as the internal portion 42 threads.

C. Specific Configuration of the Internal Portion 42 and the External Portion 44

The specific configuration of the internal portion 42 and the external portion 44 can best be seen in FIGS. 24 and 25, and as such, will be discussed with reference thereto.

(1) The Internal Portion 42.

The internal portion 42 is a slender and elongated screw 45.

The slender and elongated screw 45 of the internal portion 42 has a proximal end 46, a distal end 48, and external threads 50.

The external threads 50 of the slender and elongated screw 45 of the internal portion 42 extend axially from the proximal end 46 of the slender and elongated screw 45 of the internal portion 42 to the distal end 48 of the slender and elongated screw 45 of the internal portion 42, and are for threadably engaging into the bone 32.

The distal end 48 of the slender and elongated screw 45 of the internal portion 42 is a tapered distal end 52. The tapered distal end 52 of the distal end 48 of the slender and elongated screw 45 of the internal portion 42 is for facilitating passage through the bone 32.

The proximal end 46 of the slender and elongated screw 45 of the internal portion 42 is a screw head 54. The screw head 54 of the proximal end 46 of the slender and elongated screw 45 of the internal portion 42 has external threads 56. The external threads 56 of the screw head 54 of the proximal end 46 of the slender and elongated screw 45 of the internal portion 42 are for threadably engaging in the applicable interchangeable plate 40.

(2) The External Portion 44.

The external portion 44 is a slender, elongated, and generally cylindrically shaped sleeve 58.

The slender, elongated, and generally cylindrically shaped sleeve 58 of the external portion 44 has a proximal end 60 and a distal end 62.

The distal end 62 of the slender, elongated, and generally cylindrically shaped sleeve 58 of the external portion 44 is a tapered and/or fluted distal end 64. The tapered and/or fluted distal end 64 of the distal end 62 of the slender, elongated, and generally cylindrically shaped sleeve 58 of the external portion 44 is for facilitating passage through the bone 32 during threading of the slender and elongated screw 45 of the internal portion 42 into the bone 32.

The proximal end 60 of the slender, elongated, and generally cylindrically shaped sleeve 58 of the external portion 44 is a ring-like proximal end 66.

The ring-like proximal end 66 of the proximal end 60 of the slender, elongated, and generally cylindrically shaped sleeve 58 of the external portion 44 is defined at least by a shoulder 72.

The internal portion 42 sits axially in the external portion 44, with the screw head 54 of the proximal end 46 of the slender and elongated screw 45 of the internal portion 42 threading coaxially in the applicable interchangeable plate 40.

The external portion 44 further has at least one fin 74. The at least one fin 74 of the external portion 44 extends axially from the tapered and/or fluted distal end 64 of the distal end 62 of the slender, elongated, and generally cylindrically shaped sleeve 58 of the external portion 44 to past the ring-like proximal end 66 of the proximal end 60 of the slender, elongated, and generally cylindrically shaped sleeve 58 of the external portion 44 so as to be flush with the screw head 54 of the proximal end 46 of the slender and elongated screw 45 of the internal portion 42.

That portion 76 of the at least one fin 74 of the external portion 44 extending upwardly from the ring-like proximal end 66 of the proximal end 60 of the slender, elongated, and generally cylindrically shaped sleeve 58 of the external portion 44 to flush with the screw head 54 of the proximal end 46 of the slender and elongated screw 45 of the internal portion 42 extends divergently upwardly so as to form at least one diverging fin extension 78.

The at least one diverging fin extension 78 of the at least one fin 74 of the external portion 44 is adjacent to the screw head 54 of the proximal end 46 of the slender and elongated screw 45 of the internal portion 42 and rests in at least one tapered cutout 82 of the specifically configured through bore 80 in the applicable interchangeable plate 40, respectively.

D. Method of Utilizing the Interchangeable Orthopedic Blade 30 in Cooperation with the Applicable Interchangeable Plate 40

The method of utilizing the interchangeable orthopedic blade 30 can best be seen in FIGS. 26-29, and as such, will be discussed with reference thereto.

The method of utilizing the interchangeable orthopedic blade 30 in cooperation with the applicable interchangeable plate 40 comprises the steps of:

STEP 1: Dropping the external portion 44 through a specifically configured through bore 80 in the applicable interchangeable plate 40 until the at least one diverging fin extension 78 of the at least one fin 74 of the external portion 44 rests in at least one tapered cutout 82 of the specifically configured through bore 80 in the applicable interchangeable plate 40, respectively;

STEP 2: Dropping the slender and elongated screw 45 of the internal portion 42 through the specifically configured through bore in the applicable interchangeable plate 40 and into the external portion 44; and STEP 3: Threading the external threads 56 of the screw head 54 of the proximal end 46 of the slender and elongated screw 45 of the internal portion 42 into internal threads 84 in the specifically configured through bore 80 in the applicable interchangeable plate 40 until the screw head 54 of the proximal end 46 of the slender and elongated screw 45 of the internal portion 42 bottoms out against the ring-like proximal end 66 of the proximal end 60 of the slender, elongated, and generally cylindrically shaped sleeve 58 of the external portion 44, to thereby lock the interchangeable orthopedic blade 30 in place on the applicable interchangeable plate 40.

E. Introductory—Second Embodiment

Referring now to FIG. 30, the interchangeable orthopedic blade of the embodiments of the present invention is shown generally at 130 for more accurately placing in, without excessive damage to, a bone 132 when repairing a fracture 134 in the bone 132 so as to provide absolute stable fixation by holding the fracture 134 in its anatomic position and resist applied forces while healing, to thereby provide a stable anatomic restoration and eliminate a need for revision surgery due to failure of fixation or malunion, and for further cooperating with an applicable interchangeable plate 140.

F. Overall Configuration of the Second Embodiment of the Interchangeable Orthopedic Blade 130

The overall configuration of the second embodiment of the interchangeable orthopedic blade 130 can best be seen in FIG. 31, and as such, will be discussed with reference thereto.

The interchangeable orthopedic blade 130 comprises an internal portion 142 and an external portion 144.

The internal portion 142 is received in the external portion 144. The internal portion 142 rotates relative to the external portion 144, and the external portion 144 moves non-rotatably axially into the bone 132.

G. Specific Configuration of the Internal Portion 142 and the External Portion 144

The specific configuration of the internal portion 142 and the external portion 144 can best be seen in FIGS. 32 and 33, and as such, will be discussed with reference thereto.

(1) The Internal Portion 142.

The internal portion 142 is a fastener 144a. The fastener 144a of the internal portion 142 is an externally threaded set screw 144c. The externally threaded set screw 144c of the fastener 144a of the internal portion 142 threads into the applicable interchangeable plate 140 locking the external portion 144 from backing out.

(2) The External Portion 144.

The external portion 144 is a slender, elongated, and generally cylindrically shaped sleeve 158.

The slender, elongated, and generally cylindrically shaped sleeve 158 of the external portion 144 has a proximal end 160 and a distal end 162.

The distal end 162 of the slender, elongated, and generally cylindrically shaped sleeve 158 of the external portion 144 is a tapered and/or fluted distal end 164. The tapered and/or fluted distal end 164 of the distal end 162 of the slender, elongated, and generally cylindrically shaped sleeve 158 of the external portion 144 is for facilitating passage through the bone 132.

The proximal end 160 of the slender, elongated, and generally cylindrically shaped sleeve 158 of the external portion 144 is a ring-like proximal end 166.

The ring-like proximal end 166 of the proximal end 160 of the slender, elongated, and generally cylindrically shaped sleeve 158 of the external portion 144 is defined at least by a shoulder 172.

The internal portion 142 sits axially in the external portion 144, with the externally threaded set screw 144c of the fastener 144a of the internal portion 142 threading coaxially into the applicable interchangeable plate 140.

The external portion 144 further has at least one fin 174. The at least one fin 174 of the external portion 144 extends axially from the tapered and/or fluted distal end 164 of the distal end 162 of the slender, elongated, and generally cylindrically shaped sleeve 158 of the external portion 144 to past the ring-like proximal end 166 of the proximal end 160 of the slender, elongated, and generally cylindrically shaped sleeve 158 of the external portion 144 so as to be flush with the externally threaded set screw 144c of the fastener 144a of the internal portion 142.

That portion 176 of the at least one fin 174 of the external portion 144 extending upwardly from the ring-like proximal end 166 of the proximal end 160 of the slender, elongated, and generally cylindrically shaped sleeve 158 of the external portion 144 to flush with the externally threaded set screw 144c of the fastener 144a of the internal portion 142 extends divergently upwardly so as to form at least one diverging fin extension 178.

The at least one diverging fin extension 178 of the at least one fin 174 of the external portion 144 is adjacent to the externally threaded set screw 144c of the fastener 144a of the internal portion 142 and rests in at least one tapered cutout 182 of the specifically configured through bore 180 in the applicable interchangeable plate 140, respectively.

The externally threaded set screw 144c of the fastener 144a of the internal portion 142 threads coaxially into the applicable interchangeable plate 140, rests against the at least a shoulder 172 of the ring-like proximal end 166 of the proximal end 160 of the slender, elongated, and generally cylindrically shaped sleeve 158 of the external portion 144, and is adjacent to the at least one diverging fin extension 178 of the at least one fin 174 of the external portion 144.

H. Method of Utilizing the Interchangeable Orthopedic Blade 130 in Cooperation with the Applicable Interchangeable Plate 140

The method of utilizing the interchangeable orthopedic blade 130 can best be seen in FIG. 33, and as such, will be discussed with reference thereto.

The method of utilizing the interchangeable orthopedic blade 130 in cooperation with the applicable interchangeable plate 140 comprises the steps of:

STEP 1: Dropping the external portion 144 through the specifically configured through bore 180 in the applicable interchangeable plate 140 until the at least one diverging fin extension 178 of the at least one fin 174 of the external portion 144 rests in at least one tapered cutout 182 of the specifically configured through bore 180 in the applicable interchangeable plate 140, respectively;

STEP 2: Dropping the externally threaded set screw 144c of the fastener 144a of the internal portion 142 into the specifically configured through bore 180 in the applicable interchangeable plate 140; and STEP 3: Threading the externally threaded set screw 144c of the fastener 144a of the internal portion 142 into internal threads 184 in the specifically configured through bore 180 in the applicable interchangeable plate 140 until the externally threaded set screw 144c of the fastener 144a of the internal portion 142 bottoms out against the ring-like proximal end 166 of the proximal end 160 of the slender, elongated, and generally cylindrically shaped sleeve 158 of the external portion 144, to thereby lock the interchangeable orthopedic blade 130 in place on the applicable interchangeable plate 140.

I. Impressions

It will be understood that each of the elements described above or two or more together may also find a useful application in other types of constructions differing from the types described above.

While the embodiments of the present invention have been illustrated and described as embodied in an interchangeable orthopedic blade for more accurately placing in, without excessive damage to, a bone when repairing a fracture in the bone by cooperating with an interchangeable orthopedic plate, so as to provide absolute stable fixation by holding the fracture in its anatomic position and resist applied forces while healing, to thereby provide a stable anatomic restoration and eliminate a need for revision surgery due to failure of fixation or malunion, nevertheless, they are not limited to the details shown, since it will be understood that various omissions, modifications, substitutions, and changes in the forms and details of the embodiments of the present invention illustrated and their operation can be made by those skilled in the art without departing in any way from the spirit of the embodiments of the present invention.

Without further analysis, the foregoing will so fully reveal the gist of the embodiments of the present invention that others can by applying current knowledge readily adapt them for various applications without omitting features that from the standpoint of prior art fairly constitute characteristics of the generic or specific aspects of the embodiments of the present invention.

The invention claimed is:

1. An interchangeable orthopedic blade for more accurately placing in, without excessive damage to, a bone when repairing a fracture in the bone so as to provide absolute stable fixation by holding the fracture in its anatomic position and resist applied forces while healing, to thereby provide a stable anatomic restoration and eliminate a need for revision surgery of fixation or malunion, and for further cooperating with an applicable interchangeable plate, said interchangeable orthopedic blade comprising:
  a) an internal portion; and
  b) an external portion;
  wherein said internal portion is for more accurately placing said interchangeable orthopedic blade in, without excessive damage to, the bone when repairing the fracture in the bone and ultimately providing absolute stable fixation by said interchangeable orthopedic blade holding the fracture in its anatomic position and resisting applied forces while healing, to thereby provide the stable anatomic restoration and eliminate the need for revision surgery due to failure of fixation or malunion;
  wherein said internal portion is received in said external portion;
  wherein said internal portion is configured to rotate relative to said external portion, and cause said external portion to move non-rotatably axially with said internal portion into the bone as said internal portion threads;
  wherein said internal portion is an elongated screw;
  wherein said elongated screw of said internal portion has:
  a) a proximal end;
  b) a distal end; and
  c) external threads;
  wherein said proximal end of said elongated screw of said internal portion is a screw head;
  wherein said screw head of said proximal end of said elongated screw of said internal portion has external threads; and
  wherein said external threads of said screw head of said proximal end of said elongated screw of said internal portion are for threadably engaging in said applicable interchangeable plate;
  wherein said external portion is an elongated, and generally cylindrically shaped sleeve;
  wherein said elongated and generally cylindrically shaped sleeve of said external portion has:
  a) a proximal end; and
  b) a distal end;
  wherein said distal end of said elongated and generally cylindrically shaped sleeve of said external portion is at least one of a tapered distal end and a fluted distal end;
  wherein said at least one of said tapered distal end and said fluted distal end of said distal end of said elongated and generally cylindrically shaped sleeve of said external portion is for facilitating passage through the bone during threading of said elongated screw of said internal portion into the bone;
  wherein said proximal end of said elongated and generally cylindrically shaped sleeve of said external portion is a ring-like proximal end;
  wherein said ring-like proximal end of said proximal end of said and generally cylindrically shaped sleeve of said external portion is defined at least by a shoulder;
  wherein said external portion has at least one fin; and
  wherein a portion of said at least one fin of said external portion extends radially outwardly from said ring-like proximal end of said proximal end of said elongated and generally cylindrically shaped sleeve of said external portion to be flush with said screw head of said proximal end of said elongated screw of said internal portion and extends divergently radially outwardly so as to form at least one diverging fin extension.

2. The interchangeable orthopedic blade of claim 1, wherein said external threads of said elongated screw of said internal portion extend axially from said proximal end of said elongated screw of said internal portion to said distal end of said elongated screw of said internal portion; and
  wherein said external threads of said elongated screw of said internal portion are for threadably engaging into the bone.

3. The interchangeable orthopedic blade of claim 1, wherein said distal end of said elongated screw of said internal portion is a tapered distal end; and
  wherein said tapered distal end of said distal end of said elongated screw of said internal portion is for facilitating passage through the bone.

4. The interchangeable orthopedic blade of claim 1, wherein said internal portion sits axially in said external portion.

5. The interchangeable orthopedic blade of claim 1, wherein said at least one fin of said external portion extends axially from said at least one of said tapered distal end and said fluted distal end of said distal end of said elongated and generally cylindrically shaped sleeve of said external portion to said ring-like proximal end of said proximal end of said elongated and generally cylindrically shaped sleeve of said external portion so as to be flush with said screw head of said proximal end of said elongated screw of said internal portion.

6. The interchangeable orthopedic blade of claim 1, wherein said at least one diverging fin extension of said at least one fin of said external portion is adjacent to said screw head of said proximal end of said elongated screw of said internal portion; and
  wherein said at least one diverging fin extension of said at least one fin of said external portion rests in at least one tapered cutout of the specifically configured through bore in the applicable interchangeable plate, respectively.

* * * * *